United States Patent
Ellerby et al.

(10) Patent No.: US 9,245,290 B2
(45) Date of Patent: Jan. 26, 2016

(54) CASPASE INHIBITORS AND USES THEREOF

(71) Applicants: Buck Institute for Research on Aging, Novato, CA (US); The Regents of the University of California, Oakland, CA (US)

(72) Inventors: Lisa M. Ellerby, Novato, CA (US); Jonathan A. Ellman, Guilford, CT (US); Melissa J. Leyva, Berkeley, CA (US)

(73) Assignees: Buck Institute for Research on Aging, Novato, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/968,338

(22) Filed: Aug. 15, 2013

(65) Prior Publication Data

US 2014/0011847 A1 Jan. 9, 2014

Related U.S. Application Data

(62) Division of application No. 13/056,283, filed as application No. PCT/US2009/095032 on Aug. 6, 2009, now Pat. No. 8,518,942.

(60) Provisional application No. 61/086,731, filed on Aug. 6, 2008.

(51) Int. Cl.
| | |
|---|---|
| *C07D 405/12* | (2006.01) |
| *G06Q 30/06* | (2012.01) |
| *C07D 249/04* | (2006.01) |

(52) U.S. Cl.
CPC .......... *G06Q 30/0627* (2013.01); *C07D 249/04* (2013.01); *C07D 405/12* (2013.01)

(58) Field of Classification Search
None
See application file for complete search history.

(56) References Cited

U.S. PATENT DOCUMENTS

| 8,288,537 | B2 | 10/2012 | Golec et al. |
| 8,518,942 | B2 | 8/2013 | Ellerby et al. |
| 2002/0165230 | A1 | 11/2002 | Han et al. |
| 2011/0230527 | A1 | 9/2011 | Ellerby et al. |

FOREIGN PATENT DOCUMENTS

| EP | 1289993 B1 | 3/2003 |
| EP | 1910379 B1 | 4/2008 |
| EP | 2399915 A1 | 12/2011 |
| WO | WO 02/20465 | 3/2002 |
| WO | WO 2010/017408 | 2/2010 |

OTHER PUBLICATIONS

Wood et al., J. Am. Chem. Soc., vol. 127, No. 44, pp. 15521-15527 and "Supporting Information," pp. S1-S45 (2005).*
PCT International Search Report and Written Opinion dated Nov. 5, 2009 issued in PCT/US2009/053032 (WO 2010/017408).
PCT International Preliminary Report on Patentability dated Feb. 8, 2011 issued in PCT/US2009/053032 (WO 2010/017408).
US Notice of Allowance dated Apr. 25, 2013 issued in U.S. Appl. No. 13/056,283.
Bang et al. (2004) "Inhibitors of cysteine cathepsin and calpain do not prevent ultraviolet-8-induced apoptosis in human keratinocytes and Hela cells" *Arch Dermatol Res* 296:67-73 ; Abstract (One Page).
Brak et al. (2008) "Identification of a New Class of Nonpeptidic Inhibitors of Cruzain" J. Am. Chem. Soc. 130: 6404-6410.
Head et al. (2001) "Structure-based combinatorial library design: Discovery of non-peptidic inhibitors of caspases 3 and 8" *J Comput Aided Mol Des*. 15(12):1105-1117.
Lee et al. (2000) "Potent and Selective Nonpeptide Inhibitors of Caspases 3 and 7 Inhibit Apoptosis and Maintain Cell Functionality" *J. Biol. Chem.* 275(21):16007-16014.
Patterson et al. (2007) "Substrate activity screening (SAS): a general procedure for the preparation and screening of a fragment-based non-peptidic protease substrate library for inhibitor discovery" *Nature Protocols* 2(2): 424-433.
Wood et al. (2005) "Substrate activity screening: a fragment-based method for the rapid identification of nonpeptidic protease inhibitors." *J. Am. Chem. Soc.* 127(44):15521-15527.
Wu et al. (2003) "Development and Characterization of Nonpeptidic Small Molecule Inhibitors of the XIAP/Caspase-3 Interaction" *Chem Biol.* 10(8): 759-767.
Yang et al. (2004) "A novel systemically active caspase inhibitor attenuates the toxicities of MPTP, malonate, and 3NP in vivo" *Neurobiology of Disease* 17: 250-259.

* cited by examiner

*Primary Examiner* — Alicia L Otton
(74) *Attorney, Agent, or Firm* — Tom Hunter; Weaver Austin Villeneuve & Sampson LLP

(57) ABSTRACT

This invention provides novel caspase inhibitors useful for prophylaxis or treatment of a number of pathologies, including, for example, Huntington's disease. In certain embodiments the inhibitors include inhibitors of casepase-3 and/or casepase-6.

8 Claims, 15 Drawing Sheets

| Antibody Production | Rabbit # | | Peptide Injected | Immunoreactive to cleavage product |
|---|---|---|---|---|
| neoHtt513-1 | 98768 | | KLH-LQADSVD | yes, Ellerby production 2001, no 2006 |
| neoHtt513-2 | D8600 | D8601* | KHL-TLQADSVD | yes, purified |
| neoHtt513-3 | D7896 | D7897 | KHL-HTLQADSVD | no |
| neoHtt513-4 | D8602 | D8604 | KLH-DHTLQADSVD | no |
| neoHtt552-1 | D7959 | D7960* | KLH-CPAMDLND | yes, purified |
| neoHtt552-2 | D7962* | D8896* | KHL-CDPAMDLND | yes, purified |
| neoHtt552-3 | D8605 | D8606 | KHL-CSDPAMDLND | yes, purified |
| neoHtt552-4 | D8297 | D8298 | KHL-CPSDPAMDLND | yes, purified, monoclonal production |
| neoHtt586-1 | D8899* | D8900* | KHL-CSSEIVLD | yes, purified |
| neoHtt586-2 | D8901 | D8902 | KHL-CDSSEIVLD | yes, purified |
| noeHtt586-3 | D8903 | D8904* | KHL-CSDSSEIVLD | yes, purified |
| neoHtt586-4 | D8905* | D8906* | KHL-CPSDSSEIVLD | yes, purified, monoclonal production |

*Fig. 13B*

CASPASE INHIBITORS AND USES THEREOF

CROSS-REFERENCE TO RELATED APPLICATIONS

This application is a Divisional of U.S. Ser. No. 13/056,283, filed on May 23, 2011, which is a 371 National Phase of PCT/US2009/053032, filed on Aug. 6, 2009, which claims benefit of and priority to U.S. Ser. No. 61/086,731, filed on Aug. 6, 2008, all of which are incorporated herein by reference in their entirety for all purposes.

STATEMENT OF GOVERNMENTAL SUPPORT

This work was supported in part by Grant Nos: NS40251 and GM54051 from the National Institutes of Health. The Government has certain rights in this invention.

FIELD OF THE INVENTION

The present invention relates to caspase inhibitors and uses thereof. In certain embodiments the invention pertains to caspase-6 and/or caspase-3 inhibitors and their use in the prophylaxis and/or treatment of Huntington's disease and other neurological disorders.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally Golstein (1998) *Science* 281: 1283-1312, and Ellis et al. (1991) *Ann. Rev. Cell. Biol.*, 7: 663)

Caspases are a family of cysteine protease enzymes that are key mediators in the signaling pathways for apoptosis and cell disassembly (see, e.g., Thornberry (1998) *Chem. Biol.*, 5: R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock (see, e.g., Yaoita et al. (1998) *Circulation*, 97: 276-281; Endres et al. (1998) *J. Cerebral Blood Flow and Metabolism*, 18: 238-247; Cheng et al. (1998) *J. Clin. Invest.*, 101: 1992-1999; Yakovlev et al. (1997) *J. Neurosci.* 17: 7415-7424; Rodriquez et al. (1996) J. Exp. Med., 184: 2067-2072; and Grobmyer et al. (1999) *Mol. Med.*, 5: 585). Due to their peptidic nature, however, such inhibitors are typically characterized by undesirable pharmacological properties, such as poor cellular penetration and cellular activity, poor oral absorption, poor stability and rapid metabolism (see, e.g., Plattner and Norbeck (1990), Pp. 92-126 In: *Drug Discovery Technologies*, C. R. Clark and W. H. Moos, Eds. Ellis Horwood, Chichester, England, 1990). This has hampered their development into effective drugs.

SUMMARY OF THE INVENTION

This invention pertains to the discovery of novel non-peptidic caspase inhibitors and to uses thereof (e.g., in the prophylaxis and/or treatment of Huntington's disease or other polyglutamine diseases).

Accordingly in certain embodiments a caspase inhibitor is provided where the inhibitor has the formula of Formula I or its pharmaceutically acceptable salt where $R^1$, $R^2$, and $R^3$ of formula I are independently selected from the group consisting of H, alkyl, aryl, and heteroaryl; X of Formula I is present or absent, and when present is selected from the group consisting of CO, $SO_2$, and $CONR^4$ where $R^4$ is selected from the group consisting of H, alkyl, aryl, and heteroaryl; and Ar of Formula I is a substituted or unsubstituted aromatic or heteroaromatic ring; and the inhibitor partially or fully inhibits the activity of one or more caspases (e.g., caspase-3 and/or caspase-6). In certain embodiments the inhibitor preferentially inhibits caspase-3 and/or caspase-6 as compared to other caspases. In certain embodiments Ar is a substituted aromatic or heteroaromatic. In certain embodiments Ar is a halogen substituted aromatic or heteroaromatic. In certain embodiments Ar is a fluorine substituted aromatic or heteroaromatic (e.g., 1,2,4,5-tetrafluorophenyl). In certain embodiments, $R^2$ of Formula I is H or methyl. In certain embodiments $R^3$ is cyclohexyl. In certain embodiments $R^3$ is aryl. In certain embodiments $R^1$—X— has the formula of Formula II, Formula III, or Formula IV. In certain embodiments the inhibitor has a formula of compound MJL-003i, MJL-002i, or MJL-001i in FIG. 9. In certain embodiments the inhibitor is in a pharmaceutically acceptable carrier. In certain embodiments the inhibitor is formulated for administration to a mammal via a route selected from the group consisting of oral administration, injection, inhalation, rectal administration, transdermal administration, intranasal administration, intracerebroventricular pump, and subcutaneous depot administration. In certain embodiments the inhibitor is formulated as a unit dosage formulation.

In various embodiments methods are provided for inhibiting a caspase in a mammal. The methods typically involve comprising administering to the mammal one or more caspase inhibitors as described herein in an amount to partially or fully inhibit the activity of a caspase in a target tissue in the mammal. In certain embodiments the caspase is one or more caspases selected from the group consisting of caspase-1, caspase-3, caspase-5, caspase-6, caspase-7, caspase-8, and caspase-9. In certain embodiments the caspase is one or more caspases selected from the group consisting of caspase-1, caspase-3, and caspase-6. In certain embodiments the caspase is caspase-3 and/or caspase-6. In certain embodiments the target tissue comprises a neurological tissue (e.g., spinal cord, brain tissue, peripheral nerve tissue, etc.). In certain embodiments the inhibiting comprises preferential inhibiting of caspase-3 and/or caspase-6 as compared to other caspases. In certain embodiments the mammal is a human diagnosed with a condition selected from the group consisting of a polyglutamine disease, Parkinson's disease, Alzheimer's disease, ALS (amylotrophic lateral sclerosis), ischemia resulting from stroke, traumatic brain injury, and spinal cord injury. In certain embodiments the mammal is a human diagnosed as having or at risk for a disease selected from the group consisting of Spinobulbar muscular atrophy (Kennedy disease), Huntington disease, Dentatorubral-pallidoluysian atrophy (Haw River syndrome), Spinocerebellar ataxia type 1 (SCA-1), Spinocerebellar ataxia type 2 (SCA-2), Spinocerebellar ataxia type 3 (Machado-Joseph disease), Spinocerebellar ataxia type 6, Spinocerebellar ataxia type 7, and Spinocerebellar ataxia type 17.

Methods are also provided for mitigating one or more symptoms of a pathology characterized by abnormal apoptosis of cells in a mammal. The methods typically involve administering to the mammal one or more caspase inhibitors described herein in an amount to partially or fully mitigate the one or more symptoms. In certain embodiments the mammal is a human. In certain embodiments the mammal is a human diagnosed with a condition selected from the group consisting of a polyglutamine disease, Parkinson's disease, Alzheimer's disease, ALS (amylotrophic lateral sclerosis), ischemia resulting from stroke, traumatic brain injury, and spinal cord injury. In certain embodiments the mammal is a human diagnosed as having or at risk for a disease selected from the group consisting of Spinobulbar muscular atrophy (Kennedy disease), Huntington disease, Dentatorubral-pallidoluysian atrophy (Haw River syndrome), Spinocerebellar ataxia type 1 (SCA-1), Spinocerebellar ataxia type 2 (SCA-2), Spinocerebellar ataxia type 3 (Machado-Joseph disease), Spinocerebellar ataxia type 6, Spinocerebellar ataxia type 7, and Spinocerebellar ataxia type 17.

In another embodiment, a method of partially or fully inhibiting the onset and/or progression of Huntington's disease (or other polyglutamine diseases) is provided. The method typically involves administering to a subject having or at risk for Huntington's (or other polyglutamine disease) one or more caspase inhibitors as described herein.

In certain embodiments protease (e.g., caspase) substrates are provided. In various embodiments the substrates comprise a substrate according to formula VII or its pharmaceutically acceptable salt where $R^5$, $R^6$, $R^7$, and $R^8$ are independently selected from the group consisting of COOH, $CH_2COOH$, H, OH, $CH_3$, Cl, F, I, alkyl, alkoxy, aryl, heteroaryl, cycloalkyl, heterocycle, substituted alkyl, substituted cycloalkyl, and substituted heterocycle; R is alkyl, alkoxy, aryl, heteroaryl, cycloalkyl, heterocycle, substituted alkyl, substituted cycloalkyl, and substituted heterocycle; and the substrate is ineffectively or efficiently cleaved by a caspase selected from the group consisting of caspase-1, caspase-2, caspase-3, caspase-5, caspase-6, caspase-7, caspase-8, and caspase-9. In certain embodiments R is an R group selected from the R groups listed in Table 3, Table 4, Table 5, Table 6, Table 7, and Table 8. In certain embodiments $R^5$ is selected from the group consisting of $CH_2COOH$, COOH, and OH. In certain embodiments $R^5$ is COOH. In certain embodiments $R^6$ is selected from the group consisting of $CH_2COOH$, COOH, and OH. In certain embodiments $R^6$ is COOH. In certain embodiments $R^7$ and $R^8$ are independently selected from the group consisting of H, OH, and $CH_3$. In certain embodiments $R^7$ and $R^8$ are H. In certain embodiments the substrate comprises a molecule according to Formula VIII.

In certain embodiments methods are provided for evaluating a proteolytic substrate. The methods typically involve contacting a substrate as described herein (e.g., a substrate according to formula VII) with a protease and detecting and/or quantifying proteolytic activity the protease against the substrate. In certain embodiments the substrate is utilized as a spectrophotometric imaging tool to determine cleavage efficiency against a caspase. In certain embodiments the caspase is one or more caspases selected from the group consisting of caspase-1, caspase-3, caspase-5, caspase-6, caspase-7, caspase-8, and caspase-9. In certain embodiments R and $R^5$ of said substrate provides useful information for determining the optimal structure inhibitors.

DEFINITIONS

The term halogen refers to a nonmetal element from Group 17 (old-style: VII or VIIA; Group 7 IUPAC Style) of the periodic table, comprising fluorine, F; chlorine, Cl; bromine, Br; iodine, I; and astatine.

The term "alkyl" used herein refers to a $C_1$-$C_6$ straight or branched saturated hydrocarbon group, including, for example, methyl, ethyl, n-propyl, iso-propyl, n-butyl, sec-butyl, iso-butyl, tert-butyl, etc. In addition, "alkyl" includes substituted alkyl, cycloalkyl, and substituted cycloalkyl groups.

The term "cycloalkyl" refers to a $C_3$-$C_8$, preferably a $C_3$-$C_6$ non-aromatic hydrocarbon ring, including, for example, cyclopropyl, cyclobutyl, cyclopentyl, cyclohexyl, etc.

Substituted alkyl, cycloalkyl, or heterocyclyl refer to alkyl, cycloalkyl, or heterocyclyl wherein up to three H atoms in each residue are replaced with halogen, haloalkyl, hydroxy, lower alkoxy, carboxy, carboxalkoxy, carboxamido, cyano, carbonyl, nitro, primary amino, secondary amino, alkylthio, sulfoxide, sulfone, acylamino, acyloxy, amidino, phenyl, benzyl, heteroaryl, phenoxy, benzyloxy, heteroaryloxy, or substituted phenyl, benzyl, heteroaryl, phenoxy, benzyloxy, or heteroaryloxy.

The term "aryl" refers to a $C_1$-$C_{14}$ mono- or poly-cyclic aromatic ring, including, but not limited to, phenyl, napthyl and the like. The aryl can be unsubstituted or have one or more substituent groups wherein the substituent group can include, for example, halogen, $C_{1-6}$ alkyl, $C_{1-6}$ halogenoalkyl, $C_{1-6}$ alkoxy, amino group, etc.

The term "heteroaryl" means a 5 to 15 membered aromatic radical which has one or more heteroatoms selected from O, N or S, preferably 1 or 2 heteroatoms that are the same or different, including, for example, pyrol, pyrozol, furan, thiopen, quinoline, isoquinoline, quinazolinyl, pyridine, pyrimidine, pyrazine, pyridazine, oxazole, oxadiazole, tetrazole, thiazole, thiadiazole, imidazole, benzimidazole, benzothiapen, benzopyrol, benzofuran etc.

BRIEF DESCRIPTION OF THE DRAWINGS

FIGS. 13A, 13B, and 13C illustrate the production of Htt using neoantibodies. FIG. 13A: Diagram of identified caspase cleavage sites in Htt (SEQ ID NO:2). Caspase recognition sequences are marked in red/underlined and caspases that cleave at each site are indicated along with the amino acid number. FIG. 13B: Table of neoepitope antibodies produced to caspase cleavage sites in Htt. neoHtt513-1 injected peptide (SEQ ID NO:3), neoHtt513-2 injected peptide (SEQ ID NO:4), neoHtt513-3 injected peptide (SEQ ID NO:5), neoHtt513-4 injected peptide (SEQ ID NO:6), neoHtt552-1 injected peptide (SEQ ID NO:7), neoHtt552-2 injected peptide (SEQ ID NO:8), neoHtt552-3 injected peptide (SEQ ID NO:9), neoHtt552-4 injected peptide (SEQ ID NO:10), neoHtt586-1 injected peptide (SEQ ID NO:11), neoHtt586-2 injected peptide (SEQ ID NO:12), neoHtt586-3 injected peptide (SEQ ID NO:13), neoHtt586-4 injected peptide (SEQ ID NO:14). FIG. 13C: Diagram of the antibody recognition sequences of the four neoepitope antibodies used in this example. NeoHtt513 (SEQ ID NO:15), NeoHtt552 (SEQ ID NO:16), NeoHtt586 (SEQ ID NO:17).

FIG. 14A: Blots with full-length huntingtin (23Q) expressing cell lysates cleaved with caspase-2,-3, -6 or -7 and Htt stop constructs (23Q) ending in amino acid 513, 552 or 586 were probed with Htt antibody (2166), neoHtt513, neoHtt552 or neoHtt586. FIG. 14B: Blots with N-terminal huntingtin (amino acids 1-1212, 15Q) expressing cell lysates +/−caspase-6 were probed with a Htt antibody to amino acids 1171-1177 (left panel) or neoHtt586 (right panel). neoHtt586 has no non-specific reactivity.

DETAILED DESCRIPTION

Figure 1:
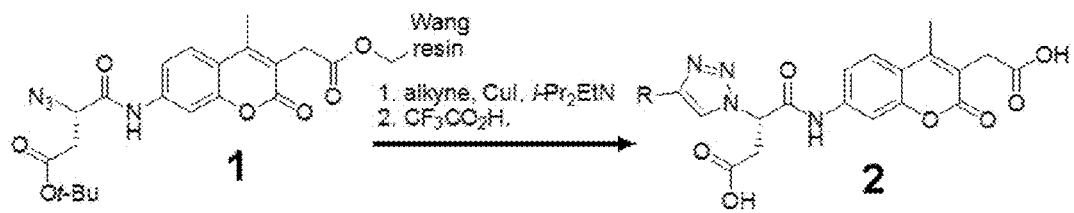
FIG. 1 illustrates the synthesis of 1,2,3-triazole substrates.

This invention pertains to the discovery of novel caspase inhibitors and to uses thereof. In certain embodiments the inhibitors inhibit caspase-3 and/or casepase-6. The inhibitors are consequently believed to be capable of inhibiting the onset and/or progression (e.g., delay the onset of and/or ameliorate the severity of) Huntington's disease.

Huntington's disease (HD) is an autosomal-dominant progressive neurodegenerative disorder leading to loss of function and viability of neurons in the striatum and cortex. Proteolysis of mutant huntingtin (Htt) is believed to be a critical molecular event triggering the selective neuronal loss. Caspase cleavage of mutant Htt has been shown to correlate with cytotoxicity in HD cell culture and mouse models and most recently, caspase-6 cleavage of mutant Htt has been shown to play a key role in HD pathogenesis in a full-length Htt mouse model of HD (YAC128; see, e.g., Graham et al. (2006) *Cell* 125: 1179-1191)).

Given the strong evidence for the "toxic fragment hypothesis" in HD, we used a fragment-based non-peptidic protease substrate library to screen for caspase-2, -3 and caspase-6 inhibitors. Substrate activity screening (SAS), a fragment-based identification method yielded novel, low-molecular weight substrates that were optimized and converted from substrates to potent, non-peptidic inhibitors of caspase-3 and caspase-6. Three illustrative inhibitors are designated: MJL-001i, MJL-002i, and MJL-003i. MJL-001i, MJL-002i, MJL-003i (1-100 nM) suppressed Hdh111Q mediated toxicity and blocked proteolysis of Htt at amino acid 513 (caspase-3 site) and 586 (caspase-6 site). Accordingly, MJL-001i, MJL-002i, and MJL-003i and related inhibitors (e.g., derivatives thereof) described herein are expected to prove effective in the prophylaxis and/or therapy for Huntington's disease.

In addition to Huntington's disease, a number of other pathologies are characterized by glutamine repeats (i.e., are polyglutamine diseases) (see, e.g., Table 1. Although the genes involved in different polyglutamine diseases have little in common, the disorders they cause follow a strikingly similar course. Each disease is characterized by a progressive degeneration of a distinct group of nerve cells. The major symptoms of these diseases are similar, although not identical, and usually affect people in midlife. Given the similarities in symptoms, the polyglutamine diseases are hypothesized to progress via common cellular mechanisms. Similarly, caspase inhibitors are believed to be effective as prophylactics or therapeutics in subjects having or at risk for these pathologies. Accordingly, in certain embodiments, the caspase inhibitors described herein are used to inhibit the onset and/or to mitigate one or more symptoms of a polyglutamine disease (e.g., Spinobulbar muscular atrophy (Kennedy disease), Huntington disease, Dentatorubral-pallidoluysian atrophy (Haw River syndrome), Spinocerebellar ataxia type 1 (SCA-1), Spinocerebellar ataxia type 2 (SCA-2), Spinocerebellar ataxia type 3 (Machado-Joseph disease), Spinocerebellar ataxia type 6, Spinocerebellar ataxia type 7, and Spinocerebellar ataxia type 17).

TABLE 1

Summary of Polyglutamine Diseases.

| Disease | Gene name | Chromosomal location | Pattern of inheritance | Protein | Normal repeat length | Disease repeat length |
|---|---|---|---|---|---|---|
| Spinobulbar muscular atrophy (Kennedy disease) | AR | Xq13-21 | X-linked recessive | androgen receptor (AR) | 9-36 | 38-62 |

TABLE 1-continued

Summary of Polyglutamine Diseases.

| Disease | Gene name | Chromosomal location | Pattern of inheritance | Protein | Normal repeat length | Disease repeat length |
|---|---|---|---|---|---|---|
| Huntington disease | HD | 4p16.3 | autosomal dominant | huntingtin | 6-35 | 36-121 |
| Dentatorubral-pallidoluysian atrophy (Haw River syndrome) | DRPLA | 12p13.31 | autosomal dominant | atrophin-1 | 6-35 | 49-88 |
| Spinocerebellar ataxia type 1 | SCA1 | 6p23 | autosomal dominant | ataxin-1 | 6-44 | 39-82 |
| Spinocerebellar ataxia type 2 | SCA2 | 12q24.1 | autosomal dominant | ataxin-2 | 15-31 | 36-63 |
| Spinocerebellar ataxia type 3 (Machado-Joseph disease) | SCA3 | 14q32.1 | autosomal dominant | ataxin-3 | 12-40 | 55-84 |
| Spinocerebellar ataxia type 6 | SCA6 | 19p13 | autosomal dominant | $\alpha 1_A$-voltage-dependent calcium channel subunit | 4-18 | 21-33 |
| Spinocerebellar ataxia type 7 | SCA7 | 3p12-13 | autosomal dominant | ataxin-7 | 4-35 | 37-306 |
| Spinocerebellar ataxia type 17 | SCA17 | 6q27 | autosomal dominant | TATA binding protein | 25-42 | 45-63 |

See, e.g., Cummings and Zoghbi 92000) *Ann. Rev. Genomics and Human Genetics* 1: 281-328; Nakamura et al. (2001) *Human Molecular Genetics* 10: 1441-1448.

In addition to Huntington's disease and other polyglutamine diseases, a number of other pathologies are characterized by activation of an apoptotic pathway. Thus, for example representative diseases mediated by caspase-3 include, but are not limited to Alzheimer's disease (see, e.g., Gervais et al. (1999) *Cell*, 97(3): 395-406; Walter et al. (1999) *Proc. Natl. Acad. Sci., USA*, 96(4): 1391-1396; Barnes et al. (1998) *J Neurosci* 18(15): 5869-5880); Parkinson's disease (see, e.g., Dodel et al. (1999) *Mol Brain Res* 64(1): 141-148; Takai et al. (1998) *J Neurosci Res.* 54(2): 214-222), ALS (amylotrophic lateral sclerosis) (see, e.g., Pasinelli et al. (1998) *Proc. Natl. Acad. Sci., USA*, 95(26): 15763-15768), AIDS (see, e.g., Kruman et al. (1998) *Exp Neurol.* 154(2): 276-288), stroke/ischemia (Hara et al. (1997) *Proc. Natl. Acad. Sci., USA*, 94(5): 2007-2012; Namura et al. (1998) *J Neurosci.* 18(10): 3659-3668; Schulz et al. 91999) *Ann Neurol.* 45(4): 421-429), traumatic brain injury (see, e.g., Yakovlev et al. (1997) *J Neurosci.* 17(19): 7415-7424; Kermer et al. (1998) *J Neurosci.* 18(12): 4656-4662; Chaudhary et al. 91999) *Mol Brain Res.* 67(1): 36-45), spinal cord injury (see, e.g., Crowe et al. 919997) *Nat Med.* 3(1): 73-76; Shuman et al. (1997) *J Neurosci Res.* 50(5): 798-808), osteoarthritis (see, e.g., Matsuo et al. (2001) *Acta. Med. Okayama*, 55(6): 333-340), etc.

Similarly, activity and/or upregulation of caspase-6 is implicated in Huntington's disease, in Alzheimer's disease (see, e.g., Guo et al. (2004) *Am. J. Pathol.* 165: 523-531; Albrecht et al. (2007) *Am J Pathol.*, 170: 1200-1209), in age-related cognitive impairment, in several neoplastic disorders including gallbladder carcinomas and dysplasias (Turunen et al. (2000) *Histol. Histopathol.*, 15: 53-60), malignant non-Hodgkin's lymphoma (Soini and Paakko (1999) *Apmis* 107: 1043-1050), breast cancer (Vakkala et al. (1999) *Br. J. Cancer* 81: 592-599) and osteosarcomas (Seki et al. (2000) *Cancer Chemother. Pharmacol.*, 45: 199-206), and the like.

In addition, it is noted that caspase-1 inhibitors are have been used as anti-inflammatory drugs (see, e.g., Randle et al. (2001) *Expert Opinion on Investigational Drugs*, 10(7): 1207-1209). Caspase-8 inhibitors have been used in the treatment of Parkinson's disease and to modulate hematopoiesis, e.g., to treat disorders characterized by hyper-proliferation of hematopoeitic cells, such as for example, leukemia (see, e.g. U.S. Patent Application No: 2007/0269419. Caspase-9 inhibitors have been used to mitigate/treat ocular neuropathologies which include, for example, acute ischemic optic neuropathy (AION), commotio retinae, glaucoma, macular degeneration, retinitis pigmentosa, retinal detachment, retinal tears or holes, diabetic retinopathy and iatrogenic retinopathy, and other ischemic retinopathies or optic neuropathies (see, e.g., PCT Application No: WO/2001/039792). Accordingly, based on the inhibitory activities reported in Table 1, the compounds of this invention are expected to prove effective in the prophylaxis and/or treatment of these conditions. Accordingly, in certain embodiments, it is contemplated to use the inhibitors described herein as a prophylactic and/or therapeutic for these and other conditions, e.g., as described above.

Caspase Inhibitors.

In various embodiments the caspase inhibitors of this invention include a caspase inhibitor of Formula I or its pharmaceutically acceptable salt:

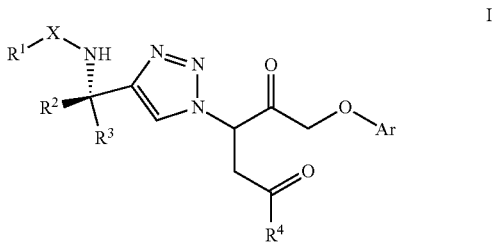

I where $R^1$, $R^2$, $R^3$, and $R^4$ are independently selected from the group consisting of H, OH, halogen, $CH_3$, $CH_2COOH$, alkyl, aryl, and heteroaryl. In various embodiments, the alkyl includes a cycloalkyl and/or a substituted alkyl; X is present or absent, and when present is selected from the group consisting of CO, $SO_2$, and $CONR^5$ where $R^5$ is selected from the group consisting of H, alkyl, aryl, and heteroaryl; and Ar is a substituted or unsubstituted aromatic or heteroaromatic ring. In various embodiments the inhibitor partially or fully inhibits the expression and/or activity of caspase-3 and/or caspase-6. In certain embodiments the inhibitor preferentially inhibits caspase-3 and/or caspase-6 as compared to other caspases. In certain embodiments Ar is a substituted aromatic or heteroaromatic (e.g., a halogen substituted aromatic or heteroaromatic). In certain embodiments, $R^4$ is H, OH, or $CH_3$. In certain embodiments, $R^4$ is OH. In certain embodiments the Ar is a fluorine substituted aromatic or heteroaromatic (e.g., 1,2,4,5-tetrafluorophenyl). In various embodiments $R^1$ is H or alkyl, and/or $R^2$ is aryl or heteroaryl.

In various embodiments $R^2$ is H or methyl, and $R^3$ is cyclohexyl. In certain embodiments, X is present and $R^1$—X— is

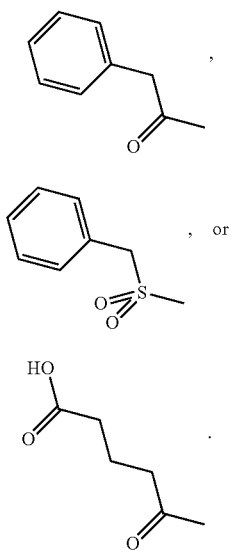

In certain embodiments $R^1$—X is formula II, III, or IV and the molecule has the formula:

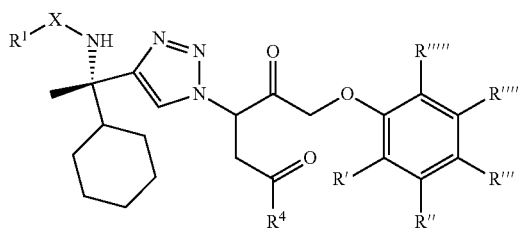

where R', R'', R''', R'''', R''''', and R'''''' are independently halogen or H.

In certain embodiments $R^1$—X is formula II, III, or IV and the molecule has the formula:

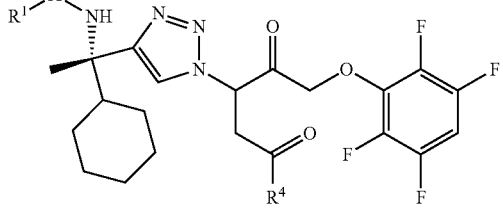

Figure 9:
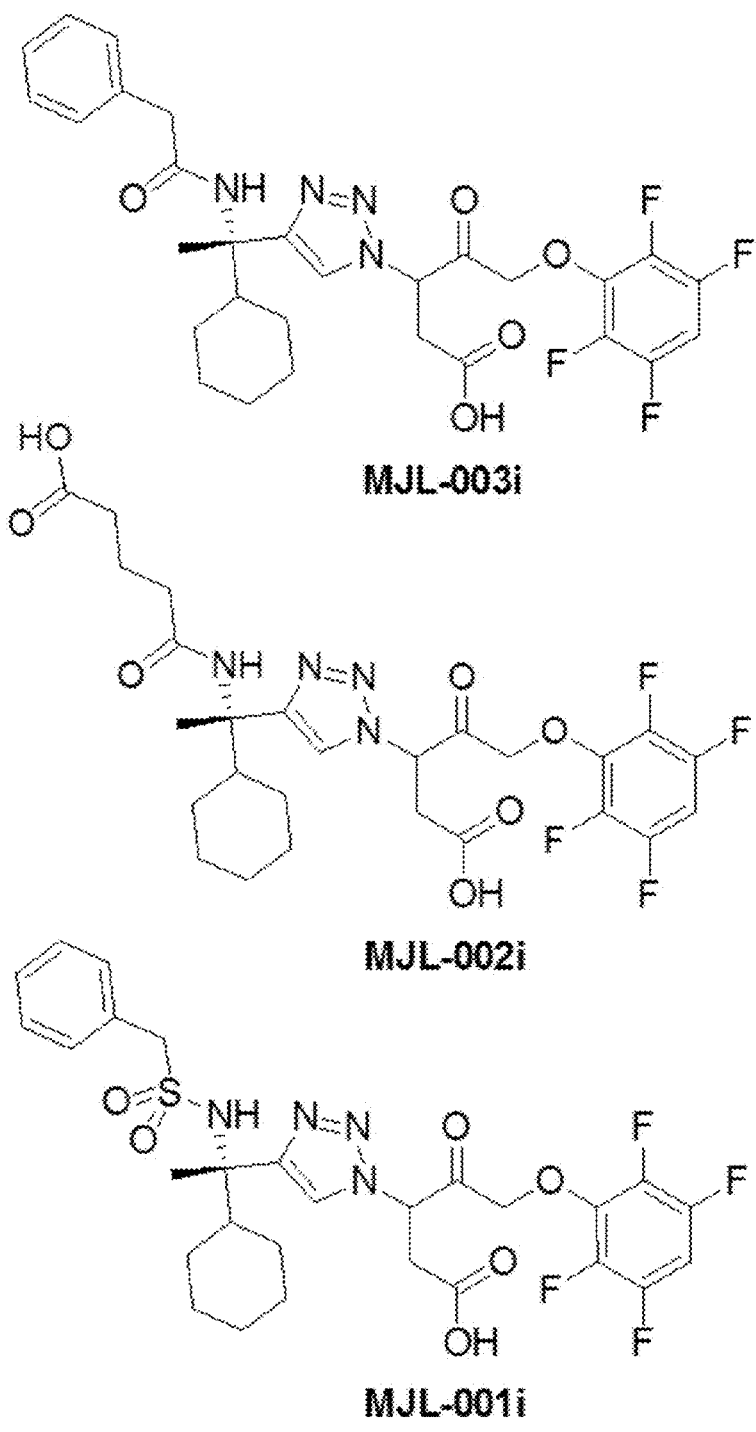
FIG. 9 shows formulas for compounds MJL-001i, MJL-002i, and MJL-003i.

Certain illustrative inhibitors of this invention include, but are not limited to compounds MJL-003i, MJL-002i, and MJL-001i as shown in FIG. 9). The activity of these illustrative caspase inhibitors of the present invention (compounds MJL-003i, MJL-002i, and MJL-001i as shown in FIG. 9) against various caspases is illustrated in Table 2.

TABLE 2

Activity of compounds MJL-003i, MJL-002i, and MJL-001i (see, e.g., FIG. 9) against caspase-1, caspase-2, caspase-3, caspase-5, caspase-6, caspase-7, caspase-8, and caspase-9.

| Caspase | MJL-003i $k_{inact}/K_i$ (s$^{-1}$/M$^{-1}$) | MJL-002i $k_{inact}/K_i$ (s$^{-1}$/M$^{-1}$) | MJL-001i $k_{inact}/K_i$ (s$^{-1}$/M$^{-1}$) |
|---|---|---|---|
| casp-1 | 55,200 ± 200 | 243,250 ± 350 | 55,200 ± 2,600 |
| casp-2[a] | 6.90 ± 0.3 | 2.0 ± 0.1 | 33.0 ± 0.5 |
| casp-3 | 29,850 ± 850 | 81,700 ± 6,900 | 47,000 ± 1,400 |
| casp-5 | 3,300 ± 200 | 16,500 ± 850 | 2,250 ± 350 |
| casp-6 | 45,750 ± 450 | 32,950 ± 1,650 | 23,100 ± 1,900 |
| casp-7 | 34,200 ± 3,800 | 57,250 ± 1,550 | 27,700 ± 2,000 |
| casp-8 | 60,000 ± 2,800 | 30,650 ± 1,950 | 82,850 ± 1,150 |
| casp-9 | 28,100 ± 2,500 | 7,550 ± 1,650 | 18,250 ± 4,050 |

Assays determining $k_{inact}/K_i$ (s$^{-1}$/M$^{-1}$) were performed in duplicate with SD values included.
[a]Assays determining $k_{ass}$ (s$^{-1}$/M$^{-1}$) were performed in duplicate with SD values included Caspase Substrates.

In certain embodiments, this invention provides caspase substrates that are effective for developing caspase inhibitors. In addition, the substrates provide can good indicators for identifying caspase activity and/or detecting the activity of other caspase inhibitors.

Figure 12:
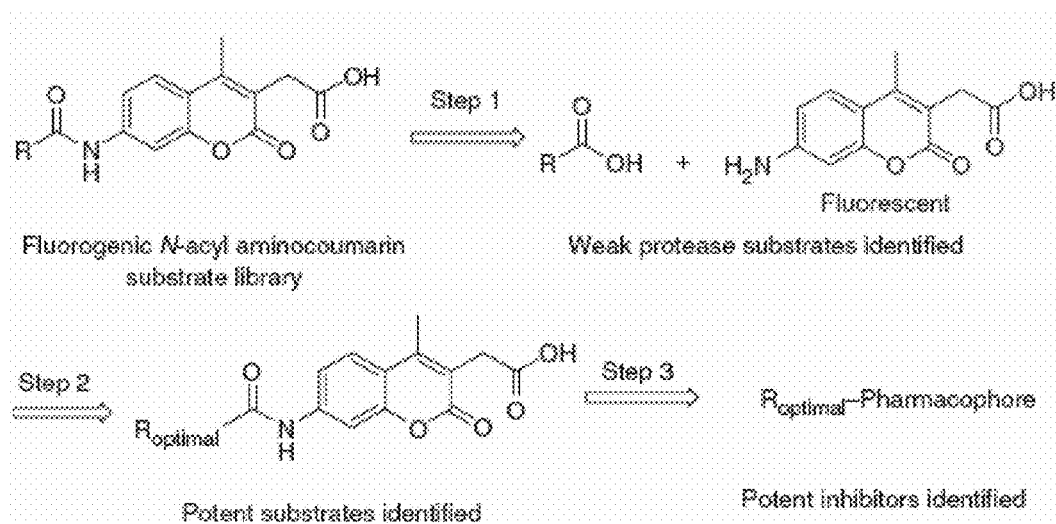
FIG. 12 shows a schematic of the SAS approach Patterson et al. (2007) *Nature Protocols* 2(2): 424.

In certain embodiments, the caspase substrates provided herein are particularly well suited for substrate activity screening, a: A Fragment-Based Method for the rapid identification of nonpeptidic protease inhibitors as described by Wood et al. (2005) *J. Am. Chem. Soc.*, 127: 15521-15527. As illustrated in FIG. 12, in certain embodiments of this approach, A library of N-acyl aminocoumarins with diverse, low molecular weight N-acyl fragments is prepared, and then in step 1, the library is screened to identify protease substrates using a one-step, high throughput fluorescence-based assay.

The substrate-based screening method in step 1 (FIG. 12) has important attributes for detecting weak binding fragments in addition to being high throughput and straightforward to perform. False positives due to aggregation, protein precipitation, or nonspecific binding are not observed because active enzyme and productive active site binding are required for protease-catalyzed amide bond hydrolysis that releases the fluorescent coumarin group. In addition, in contrast to direct binding assays and traditional inhibitor screens, catalytic substrate turnover results in signal amplification, and therefore even very weak substrates can be identified at concentrations where only minimal binding to the enzyme occurs.

Steps 2 and 3 (FIG. 12) illustrate a strategy for systematically and efficiently progressing substrates incorporating weak binding fragments into high affinity inhibitors, thereby addressing the second major challenge in fragment-based screening methods, the rapid optimization of fragments into inhibitors. In step 2, the activity of the substrates is rapidly optimized by the straightforward solid-phase synthesis and subsequent assay of focused libraries of substrate analogues. Step 3 then builds upon a key attribute of this mechanism-based substrate screen, that the N-acyl aminocoumarin must be precisely oriented in the active site to enable productive substrate cleavage, and therefore the aminocoumarin can be replaced with mechanism-based pharmacophores to directly provide protease inhibitors. The choice and versatility of pharmacophores allows reversible or irreversible inhibitors to be rapidly obtained once efficient substrates are identified.

In various embodiments the caspase inhibitors of this invention can be identified and optimized from caspase substrates of Formula V or its pharmaceutically acceptable salt:

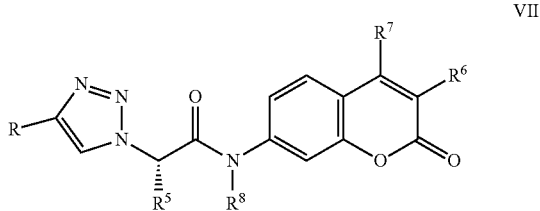

VII where $R^5$, $R^6$, $R^7$, and $R^8$ are independently selected from the group consisting of COOH, CH$_2$COOH, H, OH, CH$_3$, H, Cl, F (or other halogen), alkyl, alkoxy, aryl, heteroaryl, cycloalkyl, heterocycle, substituted alkyl, substituted cycloalkyl, and substituted heterocycle; R is alkyl, alkoxy, aryl, heteroaryl, cycloalkyl, heterocycle, substituted alkyl, substituted cycloalkyl, and substituted heterocycle; and the substrate is ineffectively or efficiently cleaved by one or more caspases selected from the group consisting of caspase-1, caspase-2, caspase-3, caspase-5, caspase-6, caspase-7, caspase-8, and caspase-9. In certain embodiments R is an R group selected from the R groups listed in Table 3, Table 4, Table 5, Table 6, Table 7, and Table 8. In certain embodiments $R^5$ is selected from the group consisting of CH$_2$COOH, COOH, and OH. In certain embodiments $R^5$ is COOH. In certain embodiments $R^6$ is selected from the group consisting of CH$_2$COOH, COOH, and OH. In certain embodiments $R^6$ is COOH. In certain embodiments $R^7$ and $R^8$ are independently selected from the group consisting of H, OH, and CH$_3$. In certain embodiments $R^7$ and/or $R^8$ are H.

In certain embodiments R is one of the R groups listed in Table 3, Table 4, Table 5, Table 6, Table 7, and/or Table 8; $R^5$ is COOH; $R^6$ is CH2COOH; and $R^7$ and $R^8$ are H (i.e., the substrate is a compound described in Table 3, Table 4, Table 5, Table 6, Table 7, and/or Table 8).

In certain embodiments, the substrate has the formula:

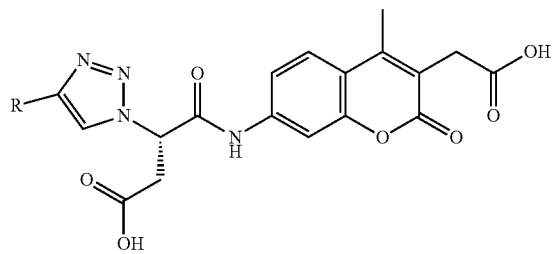

VIII where R is one of the R groups listed in Table 3, Table 4, Table 5, Table 6, Table 7, and/or Table 8;

Synthesis protocols for the caspase inhibitors and/or substrates described herein are provided in the Examples. Using the synthetic schemes provided herein, one of skill in the art can readily vary the substituents R, $R^1$, $R^2$, $R^3$, $R^4$, $R^5$, $R^6$, $R^7$, $R^8$, X, Ar, etc. with, at most, routine experimentation.

In various embodiments, for example in the SAS method described above, the aminocoumarin can be replaced with mechanism-based pharmacophores to directly provide protease inhibitors. The choice and versatility of pharmacophores allows reversible or irreversible inhibitors to be rapidly obtained once efficient substrates are identified.

Thus, for example, in certain embodiments, inhibitors are contemplated having the formula:

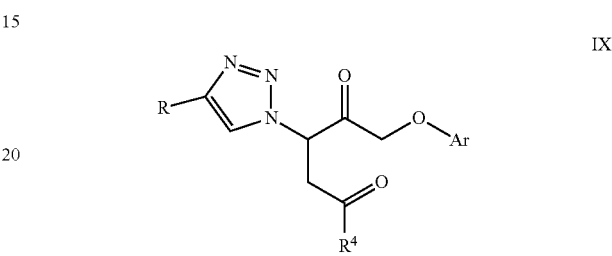

IX where R is one of the R groups listed in Table 3, Table 4, Table 5, Table 6, Table 7, and/or Table 8, $R^4$ is selected from the group consisting of H, OH, halogen, CH$_3$, CH$_2$COOH, alkyl, aryl, and heteroaryl. In certain embodiments, $R^4$ is H, OH, or CH$_3$. In certain embodiments, $R^4$ is OH. Ar is a substituted or unsubstituted aromatic or heteroaromatic ring. In certain embodiments the Ar is a fluorine substituted aromatic or heteroaromatic (e.g., 1,2,4,5-tetrafluorophenyl).

In certain embodiments, the inhibitors have the formula:

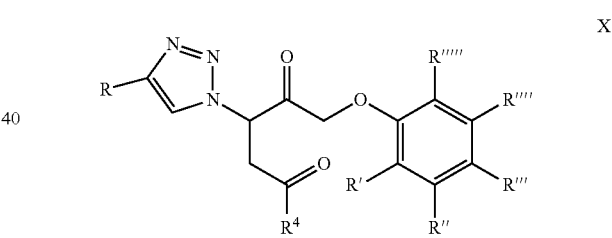

X where R is one of the R groups listed in Table 3, Table 4, Table 5, Table 6, Table 7, and/or Table 8, R', R'', R''', R'''', and R''''' are independently selected from the group consisting of halogen, and H; $R^4$ is selected from the group consisting of H, OH, halogen, CH$_3$, CH$_2$COOH, alkyl, aryl, and heteroaryl. In certain embodiments, $R^4$ is H, OH, or CH$_3$. In certain embodiments, $R^4$ is OH.

In certain embodiments, the inhibitors have the formula:

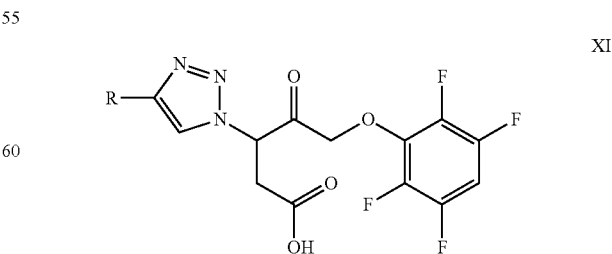

XI where R is one of the R groups listed in Table 3, Table 4, Table 5, Table 6, Table 7, and/or Table 8.

Pharmaceutical Formulations.

In order to carry out the methods of the invention (e.g., the treatment and/or prophylaxis of one or more pathologies described herein), one or more caspase inhibitors of this invention are administered, e.g. to an individual diagnosed having or at risk for Huntington's disease, Parkinson's disease, Alzheimer's disease, etc. The caspase inhibitor(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the caspase inhibitors can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the caspase inhibitors herein are halide salts, such as may be prepared using hydrochloric or hydrobromic acids. Conversely, preparation of basic salts of the caspase inhibitors of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The caspase inhibitors identified herein are useful for parenteral, topical, oral, nasal (or otherwise inhaled), rectal, or local administration such as by intracerebroventricular pump, by aerosol administration, or transdermally, for prophylactic and/or therapeutic treatment of one or more of the pathologies/indications described herein (e.g., to mitigate the onset, progression, or severity of one or more symptoms of Huntington's disease). In various embodiments the caspase inhibitor(s) are formulated as injectables for injection, delivery via an implanted catheter, and the like. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The caspase inhibitors of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the caspase inhibitor(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the caspase inhibitors, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the caspase inhibitor(s) and on the particular physio-chemical characteristics of the caspase inhibitor(s).

The excipients are preferably sterile and generally free of undesirable matter. These compositions may be sterilized by conventional, well-known sterilization techniques.

In various embodiments the caspase inhibitors described herein can be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, and/or increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, polymeric micelles, multiple emulsions, self-emulsifying, self-microemulsifying, cyclodextrins and derivatives thereof, and dendrimers.

In therapeutic applications, the compositions of this invention are administered to a patient suffering from one or more symptoms of the one or more pathologies described herein, or at risk for one or more of the pathologies described herein in an amount sufficient to prevent and/or cure and/or or at least partially prevent or arrest one or more symptoms of the disease and/or its complications. In prophylactic applications the compositions are administered to a subject diagnosed as "at risk" for the pathology in an amount sufficient to delay the onset and/or mitigate the symptoms of the disease on onset.

An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the caspase inhibitors of the formulations of this invention to effectively treat (ameliorate one or more symptoms) the patient.

The concentration of caspase inhibitor(s) can vary widely, and will be selected primarily based on fluid volumes, viscosities, body weight and the like in accordance with the particular mode of administration selected and the patient's needs (see, e.g., Remington's Pharmaceutical Science, 15th ed., Mack Publishing Company, Easton, Pa. (1980), Remington: The Science and Practice of Pharmacy, 21st Ed. 2005, Lippincott Williams & Wilkins, and the like). In certain embodiments concentrations will typically be selected to provide dosages ranging from about 0.001, 0.01, 0.1 or 1 mg/kg/day to about 5, 10, 50, or 100 mg/kg/day and sometimes higher. Typical dosages range from about 0.01 mg/kg/day to about 10 mg/kg/day, preferably from about 0.1 mg/kg/day to about 5 mg/kg/day. In certain embodiments, dosages range from about 0.01, 0.1, 1 mg, 10 mg, or 20 mg to about 50 mg injected, delivered through a catheter, a depot formulation, or given orally daily. It will be appreciated that such dosages may be varied to optimize a therapeutic regimen in a particular subject or group of subjects.

In certain preferred embodiments, the caspase inhibitors of this invention are administered orally (e.g. via a tablet) or as an injectable in accordance with standard methods well known to those of skill in the art. In other preferred embodiments, the caspase inhibitors, can also be delivered through the skin using conventional transdermal drug delivery systems, i.e., transdermal "patches" wherein the caspase inhibitor(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the caspase inhibitor(s) and any other materials that are present.

In another embodiments, the caspase inhibitor(s) can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

Kits.

In another embodiment this invention provides kits for mitigation of the onset, and/or progression, and/or severity of one or more symptoms of the pathologies described herein (e.g., Huntington's disease, Parkinson's disease, Alzheimer's disease, etc.). The kits typically comprise a container containing one or more caspase inhibitors as described herein. The inhibitor(s) can be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of the condition/pathology of interest.

In addition, the kits optionally include labeling and/or instructional materials providing directions (i.e., protocols) for the practice of the methods or use of the "therapeutics" or "prophylactics" of this invention. Preferred instructional materials describe the use of one or more active agent(s) of this invention to mitigate one or more symptoms of the pathologies described herein (e.g., Huntington's or other polyglutamine diseases) and/or to prevent the onset or increase of one or more of such symptoms in an individual at risk such. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Synthesis of Caspase Substrates, Inhibitors, and Intermediates

General Methods.

Unless otherwise noted, all chemicals were obtained from commercial suppliers and used without further purification. Wang resin was purchased from Novabiochem (San Diego). O-(7-Azabenzotriazol-1-yl)-1,1,3,3-tetramethyluronium hexafluorophosphate (HATU) was purchased from PerSeptive Biosystems (Foster City, Calif.). (S)-tert-Butanesulfinamide was provided by AllyChem Co. Ltd (Dalian, China). N-(9-Fluorenylmethoxycarbonyl)-7-amino-4-methyl-3-carboxymethylcoumarin (Fmoc-AMCA) and $N_3$-AMCA-Wang resin 1 were prepared by a previously described procedure (Wood et al. (2005) J. Am. Chem. Soc. 127: 15521-15527).

The hydrochloride salt of (S)-2-amino-2-cyclohexyl-3-butyne 30 was prepared from (S)-tert-butanesulfinamide by a previously described procedure (Patterson and Ellman (2006) *J. Org. Chem.*, 71:7110-7112). Low amine content N,N-dimethylformamide (DMF) was purchased from EM Science (Cincinnati, Ohio), and anhydrous DMF was purchased from Acros (Morris Plains, N.J.) Anhydrous THF, $CH_2Cl_2$, were obtained from Seca Solvent Systems by GlassContour and were dried over alumina under a nitrogen atmosphere. Solid-phase reactions were conducted in 12- or 35-mL polypropylene cartridges equipped with 70 mm PE frits attached to Teflon stopcocks. Cartridges and stopcocks were purchased from Applied Separations (Allentown, Pa.). Syringe barrels from 10-mL disposable syringes were used as stoppers for the 12-mL cartridges and polyethylene stoppers were used for the 35-mL cartridges. Solid phase reactions were rocked on an orbital shaker to agitate the resin. Solvents were expelled from the cartridges using pressurized air after removing the cartridge stopper and opening the stopcock. Resin was washed for a duration of 2-5 min. Solvents were removed using a Buchi rotary evaporator under reduced pressure. Reaction progress was monitored using thin-layer chromatography on Merck 60 $F_{254}$ 0.25 µm silica plates. Fmoc quantitation was performed according to literature procedure (Wood et al. (2005) *J. Am. Chem. Soc.* 127: 15521-15527). High-performance liquid chromatography (HPLC) analysis was performed with a C18 reverse phase column (4.6×100 mm) with UV detection at 220, 254, and 280 nm. Reaction progress was monitored using thin-layer chromatography on Merck 60 $F_{254}$ 0.25 µm silica plates. Liquid chromatography-mass spectrometry (LC/MS) data were obtained using a Hewlett Packard 1100 series liquid chromatography instrument and mass selective detector. $^1H$ and $^{13}C$ NMR spectra were measured with Bruker AVB-400, AVQ-400, and AV-300 spectrometers. NMR chemical shifts are reported in ppm downfield relative to the internal solvent peak, and coupling constants are reported in Hz. High-resolution mass spectra (HRMS) were performed by the University of California at Berkeley Mass Spectrometry Facility.

I. Synthesis of AMCA Substrates

A general synthesis scheme for the synthesis of 1,2,3-triazole substrates is shown in FIG. 1. Conditions: (a) alkyne, CuI, i-$Pr_2$EtN, THR rt; (b) $CF_3CO_2H$, $CH_2Cl_2$, rt.

Figure 2:
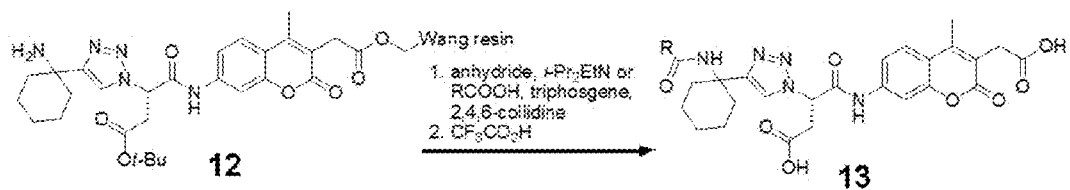
FIG. 2 illustrates the synthesis of acylated cyclohexyl amine substrates.

A general synthesis scheme for the synthesis of acylated cyclohexyl amine substrates is shown in FIG. 2

Figure 3:
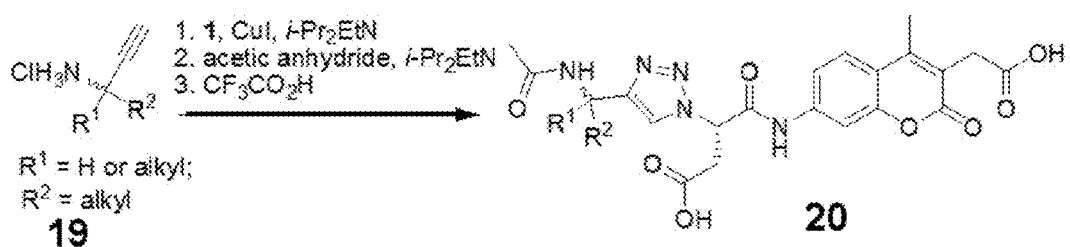
FIG. 3 illustrates a general scheme for the synthesis of substituted amide substrates.

A general synthesis scheme for the synthesis of substituted amide substrates is shown in FIG. 3. Conditions: 1, CuI, i-$Pr_2$EtN, THR rt; (b) aceticanhyddride, i-$Pr_2$EtN, THF; (c) $CF_3CO_2H$, $CH_2CL_2$, rt.

Figure 4:
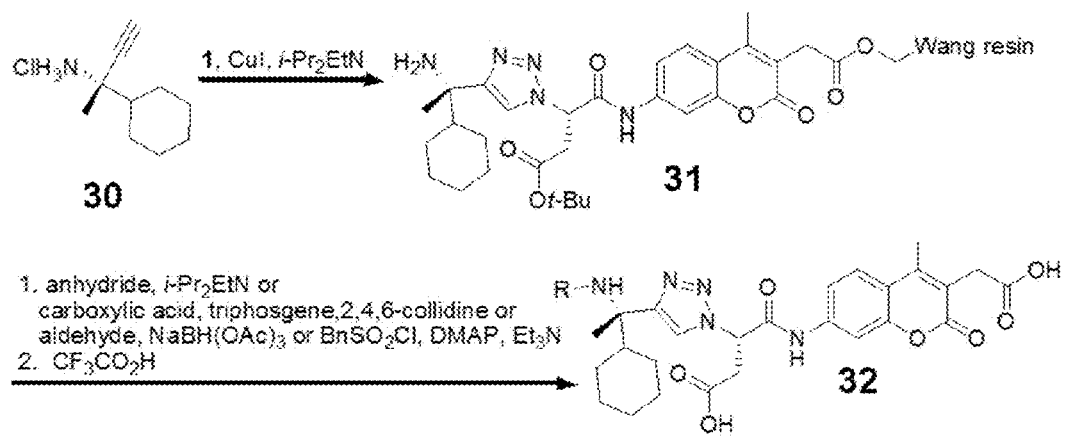
FIG. 4 illustrates a general scheme for the synthesis of functionalized cyclohexyl-methyl amine substrates.

A general synthesis scheme for the synthesis of functionalized cyclohexyl-methyl amine substrates is shown in FIG. 4.

Figure 5:
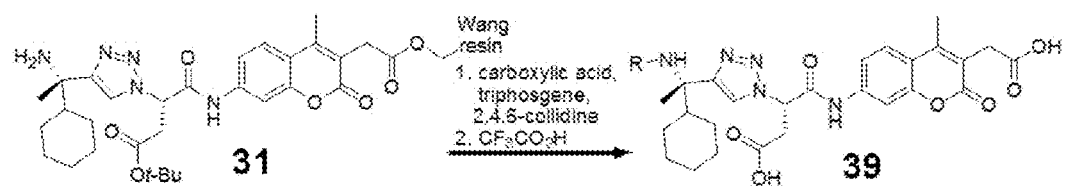
FIG. 5 illustrates scheme 5 for the synthesis of acylated benzyl substrates.

A general synthesis scheme for the synthesis of acylated benzyl substrates is shown in FIG. 5.

General Synthesis of 1,2,3-triazole-AMCA Substrates Listed in Entries 3-10 (Table 3).

Synthesis scheme 2, illustrating the synthesis of 1,2,3-Triazole Substrates is illustrated in FIG. 1.

To $N_3$-AMCA-Wang 1 resin (0.150 mmol) were added alkyne (0.02 M final concentration, 0.30 mmol, 2 equiv), i-$Pr_2$EtN (1.0 M final concentration, 15 mmol, 1.90 g, 100 equiv), and CuI (0.45 mmol, 0.09 g, 3 equiv) in THF, and the mixture was shaken for 48 h. After filtration, the resin was washed with three 10-mL portions each of THF, $CH_3OH$, THF, and $CH_2Cl_2$. The support-bound triazole product was cleaved from support and purified according to the general conditions described below. Alternatively, the support-bound triazole product was submitted to additional transformations before cleavage from support.

TABLE 3

Cleavage efficiencies of 1,2,3-triazole substrates against Caspase-3.

| Entry | R | Rel. $k_{cat}/K_m$ |
|---|---|---|
| 3 | phenethyl | 1.0 |
| 4 | benzyl | 2.0 |
| 5 | isobutyl | 2.0 |
| 6 | tert-butyl | 7.2 |
| 7 | cyclohexyl | 2.0 |
| 8 | HOOC-CH$_2$CH$_2$- | 2.0 |
| 9 | HO-CH(CH$_3$)- | 0.0 |
| 10 | 1-hydroxycyclohexyl | 7.8 |
| 11 | acetamido-cyclohexyl | 7.9 |

Cleavage and Purification Conditions.

The resin was swollen in $CH_2Cl_2$ in a cartridge. To 0.05-0.2 g of derivatized resin was added a 5 mL solution of 95% $CF_3CO_2H$, 2.5% $H_2O$, and 2.5% triisopropylsilane. The mixture was shaken for 1 h. Upon filtration, the resin was washed with the cleavage solution and three 10-mL portions of $CH_2Cl_2$. The filtrate and combined washes were concentrated under reduced pressure to yield the crude cleavage product. The crude product mixture was purified by HPLC [preparatory reverse phase C18 column (24.1×250 mm), acetonitrile/ $H_2O$-0.1% TFA; 5-95% over 50 min then maintained at 95% acetonitrile for 10 min; 10 mL/min; 254 nm detection] and lyophilized.

General Synthesis of Acylated Substrates from Anhydrides Listed in Entries 11 and 17-18 (Table 4).

Synthesis scheme 3 FIG. 2 illustrates the synthesis of acylated cyclohexyl amine substrates.

To the resin obtained above using 1-ethynyl cyclohexylamine (0.300 mmol, 0.04 g, 2.0 equiv) was added acetic, glutaric, or succinic anhydride (0.5 M final concentration, 0.750 mmol, 5 equiv) and i-$Pr_2EtN$ (1.0 M final concentration, 1.50 mmol, 0.19 g, 10 equiv) in DMF. The resulting mixture was shaken for 18 h. After filtration followed by washing with three 10-mL portions each of DMF, THF, $CH_3OH$, THF, and $CH_2Cl_2$, the substrate was cleaved from the solid support and purified using the general cleavage and purification procedures to give the desired product.

TABLE 4

Cleavage efficiencies of acylated cyclohexyl amine substrates against Caspase-3.

| Entry | R | Rel. $k_{cat}/K_m$ |
|---|---|---|
| 11 | (acetyl-NH-cyclohexyl) | 7.9 |
| 14 | (butyryl-NH-cyclohexyl) | 3.7 |
| 15 | (isobutyryl-NH-cyclohexyl) | 0.0 |

TABLE 4-continued

Cleavage efficiencies of acylated cyclohexyl amine substrates against Caspase-3.

| Entry | R | Rel. $k_{cat}/K_m$ |
|---|---|---|
| 16 | (benzoyl-NH-cyclohexyl) | 1.1 |
| 17 | (HO-succinyl-NH-cyclohexyl) | 17.3 |
| 18 | (HO-glutaryl-NH-cyclohexyl) | 62.0 |

General Synthesis of Acylated Substrates from Carboxylic Acids Listed in Entries 14-16 (Table 4).

To the resin obtained above using 1-ethynyl cyclohexylamine (0.300 mmol, 0.04 g, 2.0 equiv) was added i-$Pr_2EtN$ (1.20 mmol, 0.16 g, 8 equiv). To a THF solution of carboxylic acid (0.1 M final concentration, 0.525 mmol, 3.5 equiv) and triphosgene (0.03 M, 0.165 mmol, 0.05 g, 1.1 equiv) was added 2,4,6-collidine (0.3 M final concentration, 1.50 mmol, 0.18 g, 10 equiv). The resulting slurry was stirred for 1 min and was added to the derivatized resin. The resulting mixture was shaken for 4-12 h. After filtration, the resin was washed with three-10 mL portions of THF and the procedure was repeated two times. After filtration followed by washing with three 10-mL portions each of THF, $CH_3OH$, THF, and $CH_2Cl_2$, the substrate was cleaved from the solid support and purified using the general cleavage and purification procedures to give the desired product.

General Synthesis of Acetylated Substrates Listed in Entries 21-25 (Table 5).

The hydrochloride salts of 1-cyclohexylprop-2-yn-1-amine, 1-cyclopentylprop-2-yn-1-amine, 5-methylhex-1-yn- 3-amine were synthesized from cyclohexanecarbaldehyde, cyclopentanecarbaldehyde, 3-methylbutanal, respectively following a previously described procedure (Aschewanden et al. (2006) *Org. Lett.,* 8: 2437-2440). The hydrochloride salts of 4-methylpent-1-yn-3-amine and (S)-3,4-dimethylpent-1-yn-3-amine were synthesized from racemic and (S)-tert-Butanesulfinamide, respectively by a previously reported procedure (Patterson and Ellman (2006) *J. Org. Chem.,* 71: 7110-7112). 3-ethylpent-1-yn-3-amine and 2-methylbut-3-yn-2-amine were obtained from commercial suppliers. To the resin obtained above using the above amines or hydrochloride salts (0.300 mmol, 0.06 g, 2.0 equiv) was added acetic anhydride (0.4 M final concentration, 0.08 g, 0.750 mmol, 5 equiv) and i-Pr$_2$EtN (1.0 M final concentration, 1.50 mmol, 0.19 g, 10 equiv) in DMF. The resulting mixture was shaken for 18 h. After filtration followed by washing with three 10-mL portions each of DMF, THF, CH$_3$OH, THF, and CH$_2$Cl$_2$, the substrate was cleaved from the solid support and purified using the general cleavage and purification procedures to give the desired product.

TABLE 5

Cleavage efficiencies of substituted amide substrates.

| Cmpd | R | Rel. $k_{cat}/K_m$ |
|---|---|---|
| 11 | 1-acetamidocyclohexyl | 2.0 |
| 21 | acetamido-cyclohexylmethyl | 0.0 |
| 22 | acetamido-cyclopentylmethyl | 0.0 |
| 23 | acetamido-isobutyl | 0.0 |
| 24 | acetamido-isobutyl (variant) | 1.0 |
| 25 | acetamido-tert-butyl | 0.0 |
| 26 | acetamido-(1,1-dimethyl) | 1.0 |
| 27 | acetamido-(1-ethyl-1-methyl) | 1.0 |
| 28 | acetamido-(S)-isopropyl | 3.0 |
| 29 | acetamido-(S)-cyclohexyl | 48 |

General Synthesis of Acylated Substrates from Anhydrides Listed in Entries 29 and 34 (Table 6).

To the resin obtained above using the hydrochloride salt of (S)-2-amino-2-cyclohexyl-3-butyne 30 (0.300 mmol, 0.06 g, 2.0 equiv) was added acetic, glutaric, or succinic anhydride (0.4 M final concentration, 0.750 mmol, 5 equiv) and i-Pr$_2$EtN (1.0 M final concentration, 1.50 mmol, 0.19 g, 10 equiv) in DMF. The resulting mixture was shaken for 18 h. After filtration followed by washing with three 10-mL portions each of DMF, THF, CH$_3$OH, THF, and CH$_2$Cl$_2$, the substrate was cleaved from the solid support and purified using the general cleavage and purification procedures to give the desired product.

TABLE 6
Cleavage Efficiencies of Cyclohexyl-Methyl Amine Substrates against Caspase-3.
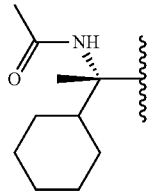 [SMILES: *[C@@](C)(NC(C)=O)C1CCCCC1]
| Entry | R | Rel. $k_{cat}/K_m$ |
|---|---|---|
| 29 | 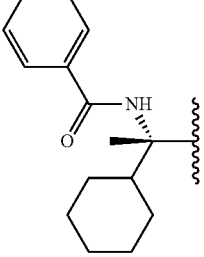 | 39.3 |
| 33 | 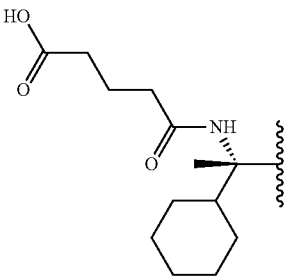 [SMILES: *[C@@](C)(NC(=O)CCCC(=O)O)C1CCCCC1] | 36.7 |
| 34 | 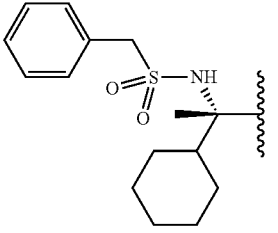 [SMILES: *[C@@](C)(NS(=O)(=O)Cc1ccccc1)C1CCCCC1] | 194 |
| 35 | 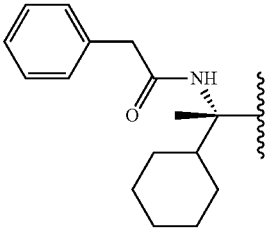 [SMILES: *[C@@](C)(NC(=O)Cc1ccccc1)C1CCCCC1] | 133 |
| 36 | 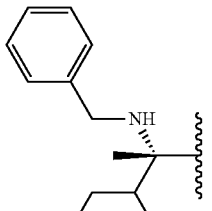 | 47 |
TABLE 6-continued
Cleavage Efficiencies of Cyclohexyl-Methyl Amine Substrates against Caspase-3.
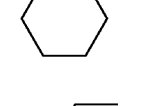
| Entry | R | Rel. $k_{cat}/K_m$ |
|---|---|---|
| 37 | 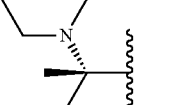 | 3.0 |
| 38 | 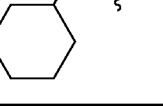 | 0.7 |
TABLE 7
Cleavage Efficiencies of AMCA Substrates against Caspase-6.
| Entry | R | Rel. $k_{cat}/K_m$ |
|---|---|---|
| 11 | 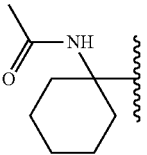 [SMILES: *C1(NC(C)=O)CCCCC1] | 0.0 |

TABLE 7-continued

Cleavage Efficiencies of AMCA Substrates against Caspase-6.

| Entry | R | Rel. $k_{cat}/K_m$ |
|---|---|---|
| 30 | (benzamide-cyclohexyl) | 1.3 |
| 31 | (HOOC-propyl-C(O)NH-cyclohexyl) | 0.0 |
| 34 | (acetamide-isobutyl) | 0.0 |
| 24 | (acetamide-isobutyl) | 0.0 |
| 32 | (acetamide-cyclohexyl) | 1.0 |
| 33 | (HOOC-propyl-C(O)NH-cyclohexyl) | 2.5 |
| 35 | (benzylsulfonamide-cyclohexyl) | 8.8 |
| 35 | (phenylacetamide-cyclohexyl) | 29 |
| 36 | (benzylamine-cyclohexyl) | 0.0 |

General Synthesis of Acylated Substrates from Carboxylic Acids Listed in Entries 33, 36, and 40-46 (Tables 6, 7, and 8).

To the resin obtained above using the hydrochloride salt of (S)-2-amino-2-cyclohexyl-3-butyne 30 (0.300 mmol, 0.06 g, 2.0 equiv) was added i-Pr$_2$EtN (1.20 mmol, 0.16 g, 8 equiv). To a THF solution of carboxylic acid (0.1 M final concentration, 0.525 mmol, 3.5 equiv) and triphosgene (0.03 M final concentration, 0.165 mmol, 0.05 g, 1.1 equiv) was added 2,4,6-collidine (0.3 M final concentration, 1.50 mmol, 0.18 g, 10 equiv). The resulting slurry was stirred for 1 min and was added to the derivatized resin. The resulting mixture was shaken for 4-12 h. After filtration, the resin was washed with three-10 mL portions of THF and procedure was repeated two times. After filtration followed by washing with three 10-mL portions each of THF, CH$_3$OH, THF, and CH$_2$Cl$_2$, the substrate was cleaved from the solid support and purified using the general cleavage and purification procedures to give the desired product.

TABLE 8

Cleavage Efficiencies of Acylated Benzyl Substrates against Casapse-6

| Entry | R | Rel. $k_{cat}/K_m$ |
|---|---|---|
| 36 | benzyl | 72 |
| 40 | 3-Ph-benzyl | 1.0 |
| 41 | MeO-benzyl | m-24 |
| 42 | | p-8.5 |
| 43 | 3-Me-benzyl | 23 |
| 45 | 3-F$_3$C-benzyl | 23 |
| 46 | 3-PhO-benzyl | 46 |
| 47 | 4-Cl-benzyl | 52 |

Synthesis of Sulfonamide Substrate, Entry 35 (Tables 6, and 7).

To the resin obtained above using the hydrochloride salt of (S)-2-amino-2-cyclohexyl-3-butyne 30 (0.300 mmol, 0.06 g, 2.0 equiv) was added phenylmethanesulfonyl chloride (0.33 mmol, 0.06 g, 1.10 equiv), DMAP (0.06 mmol, 0.007 g, 0.2 equiv), and NEt$_3$ (0.66 mmol, 0.07 g, 2.2 equiv) in CH$_2$Cl$_2$ (2.0 mL). The resulting mixture was shaken for 48 h. After filtration, the resin was washed with three-10 mL portions of THF and procedure was repeated two times. After filtration followed by washing with three 10-mL portions each of THF, CH$_3$OH, THF, and CH$_2$Cl$_2$, the substrate was cleaved from the solid support and purified using the general cleavage and purification procedures to give the desired product.

General Synthesis of Amine Substrates Listed in Entries 37-38 (Table 6).

To the resin obtained above using the hydrochloride salt of (S)-2-amino-2-cyclohexyl-3-butyne 30 (0.300 mmol, 0.06 g, 2.0 equiv) was added aldehyde (0.8 M final concentration, 1.50 mmol, 10 equiv), acetic acid (1.50 mmol, 0.09 g, 10 equiv), and NaHB(OAc)$_3$ (1.50 mmol, 0.32 g, 10 equiv) in THF. The resulting mixture was shaken for 36 h. After filtration followed by washing with three 10-mL portions each of THF, CH$_3$OH, THF, and CH$_2$Cl$_2$, the substrate was cleaved from the solid support and purified using the general cleavage and purification procedures to give the desired product.

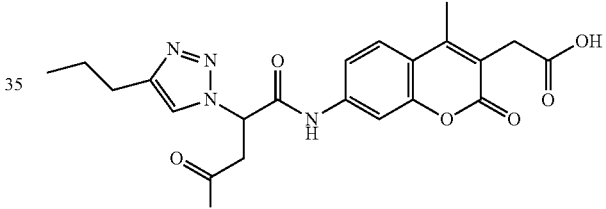

5

$^1$H NMR (400 MHz, DMSO d-6): δ 0.88-0.92 (t, 3, J=7.4), 1.58-1.62 (t, 2, J=7.2), 2.36 (s, 3), 2.54-2.61 (m, 2), 3.23-3.38 (m, 2), 3.58 (s, 2), 5.76-5.74 (t, 1, J=6.8), 7.48-7.50 (d, 1, J=8.4), 7.71 (s, 1), 7.79-7.81 (d, 1, J=8.4), 8.03 (s, 1), 10.99 (s, 1). HRMS (FAB+) m/z: 443.1567 (MH$^+$ C$_{21}$H$_{23}$N$_4$O$_7$ requires 443.1555).

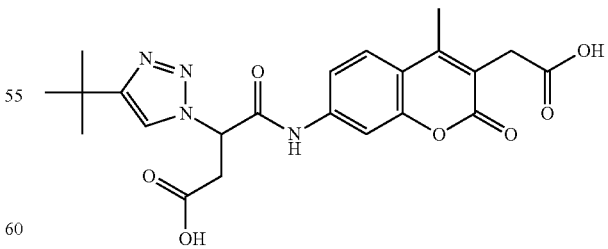

6

$^1$H NMR (400 MHz, DMSO d-6): δ 1.27 (s, 9H), 2.36 (s, 3), 3.24-3.41 (m, 2), 3.58 (s, 2), 5.73-5.76 (t, 1, J=7.4), 7.49-7.52 (d, 1, J=8.8), 7.72 (s, 1), 7.78-7.80 (d, 1, J=8.8), 8.04 (s, 1), 10.99 (s, 1). HRMS (FAB+) m/z: 457.1723 (MH$^+$ C$_{22}$H$_{25}$N$_4$O$_7$ requires 457.1713).

4

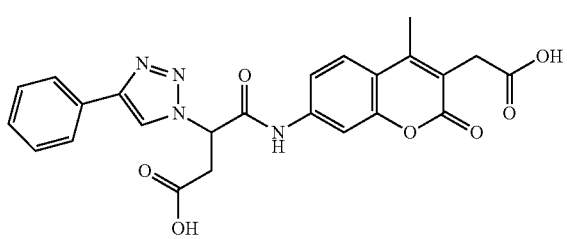

¹H NMR (400 MHz, DMSO d-6): δ 2.37 (s, 3), 3.38-3.43 (m, 2), 3.58 (s, 2), 5.86-5.89 (t, 1, J=7.2), 7.32-7.36 (t, 1, J=7.6), 7.44-7.48 (t, 2, J=7.6), 7.51-7.53 (d, 1, J=7.6), 7.73 (s, 1), 7.80-7.82 (d, 1, J=8.8), 7.87-7.88 (d, 2, J=7.6), 8.82 (s, 1), 11.01 (s, 1). HRMS (FAB+) m/z: 477.1410 (MH+ $C_{24}H_{21}N_4O_7$ requires 477.1424).

7

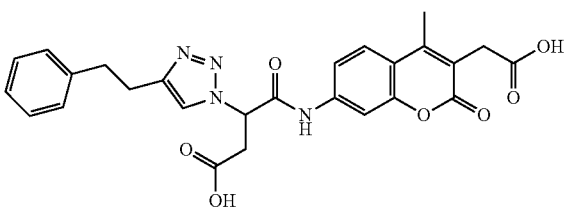

¹H NMR (400 MHz, DMSO d-6): δ 1.17-1.22 (m, 1), 1.29-1.41 (m, 4), 1.64-1.67 (m, 1), 1.69-1.73 (m, 2), 1.93-2.07 (m, 2), 2.36 (s, 3), 2.65-2.7 (m, 1), 3.22-3.39 (m, 2), 3.58 (s, 2), 5.72-5.76 (t, 1, J=7.4), 7.49-7.51 (d, 1, J=8.8), 7.72 (s, 1), 7.79-7.80 (d, 1, J=8.8), 8.01 (s, 1), 11.01 (s, 1). HRMS (FAB+) m/z: 483.1879 (MH+ $C_{24}H_{28}N_4O_7$ requires 483.1875).

3

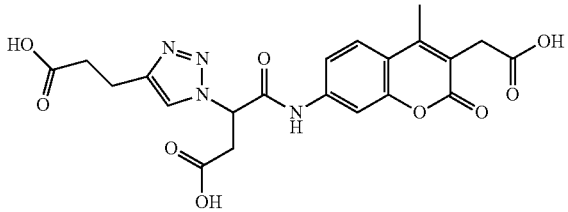

¹H NMR (400 MHz, DMSO d-6): δ 2.37 (s, 3), 2.92 (s, 4), 3.21-3.39 (m, 2), 3.59 (s, 2), 5.74-5.78 (t, 1, J=7.4), 7.14-7.17 (m, 1) 7.20-7.26 (m, 4), 7.48-7.50 (d, 1, J=8.8), 7.71 (s, 1), 7.79-7.81 (d, 1, J=8.8), 8.02 (s, 1), 11.00 (s, 1). HRMS (FAB+) m/z: 505.1723 (MH+ $C_{26}H_{25}N_4O_7$ requires 505.1737).

8

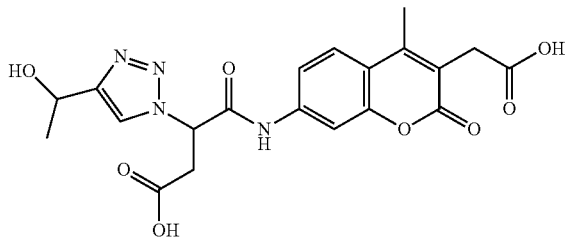

¹H NMR (400 MHz, DMSO d-6): δ 2.36 (s, 3), 2.57-2.61 (t, 2, J=7.6), 2.84-2.87 (t, 2, J=7.6), 3.21-3.39 (m, 2), 3.58 (s, 2), 5.73-5.77 (t, 1, J=7.4), 7.48-7.50 (d, 1, J=8.8), 7.71 (s, 1), 7.78-7.80 (d, 1, J=8.8), 8.04 (s, 1), 11.01 (s, 1). HRMS (FAB+) m/z: 473.1309 (MH+ $C_{21}H_{21}N_4O_7$ requires 473.1315).

9

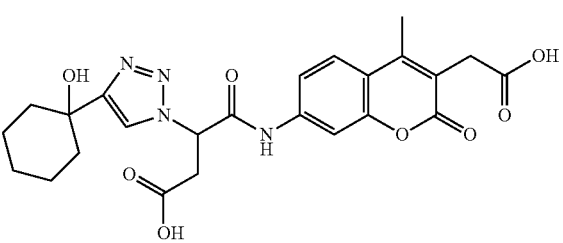

¹H NMR (400 MHz, DMSO d-6): δ 1.40-1.41 (d, 3, J=6.4), 2.37 (s, 3), 3.25-3.41 (m, 2), 3.59 (s, 2), 4.82-4.85 (t, 1, J=6.4), 5.76-5.79 (t, 1, J=7.2), 7.49-7.51 (d, 1, J=8.8), 7.71 (s, 1), 7.79-7.81 (d, 1, J=8.8), 8.09 (s, 1), 11.00 (s, 1). HRMS (FAB+) m/z: 445.1359 (MH+ $C_{20}H_{21}N_4O_8$ requires 445.1356).

10

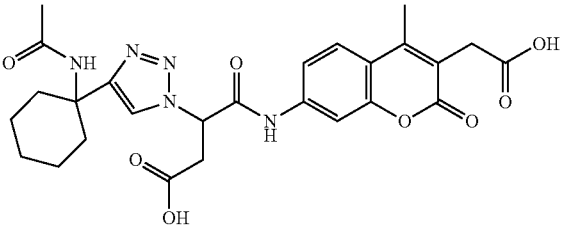

¹H NMR (400 MHz, DMSO d-6): δ 1.25-1.40 (m, 4), 1.50-1.67 (m, 4), 1.82-1.84 (m, 2), 2.37 (s, 3), 3.28-3.37 (m, 2), 3.54 (s, 2), 5.74-5.77 (t, 1, J=7.2), 7.49-7.51 (d, 1, J=8.8), 7.72 (s, 1), 7.80-7.82 (d, 1, J=8.8), 8.04 (s, 1), 11.00 (s, 1). HRMS (FAB+) m/z: 521.1648 (MNa+ $C_{24}H_{26}N_4O_8Na$ requires 521.1641).

11

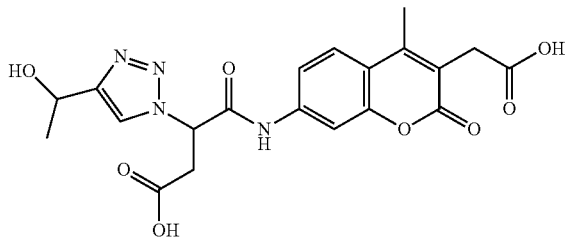

¹H NMR (400 MHz, DMSO d-6): δ 1.24-1.43 (m, 6), 1.52-1.79 (m, 2), 1.82 (s, 3), 2.27-2.34 (m, 2), 2.36 (s, 3), 3.25-3.33 (m, 2), 3.58 (s, 2), 5.69-5.73 (t, 1, J=7.2), 7.48-7.50 (d, 1, J=8.8), 7.71 (s, 1), 7.75 (s, 1), 7.79-7.81 (d, 1, J=8.8), 7.96 (s, 1), 10.99 (s, 1). HRMS (FAB+) m/z: 540.2094 (MH+ $C_{26}H_{29}N_5O_8$ requires 540.2102).

14

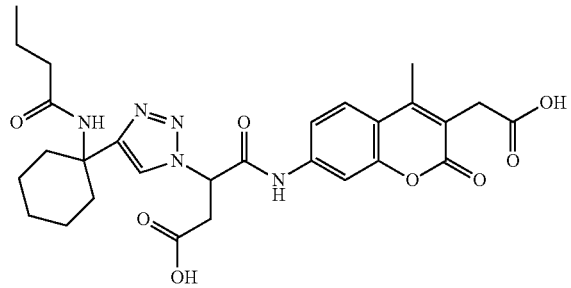

¹H NMR (400 MHz, DMSO d-6): δ 0.78-0.82 (t, 3, J=7.2) 1.21-1.33 (m, 1), 1.42-1.48 (m, 7), 1.74-1.76 (m, 2), 2.05-2.08 (t, 2, J=7.2), 2.34-2.35 (m, 2), 2.36 (s, 3), 3.21-3.42 (m, 2), 3.52 (s, 2), 5.69-5.71 (t, 1, J=7.4), 7.48-7.50 (d, 1, J=8.8), 7.67 (s, 1), 7.71 (s, 1), 7.79-7.82 (d, 1, J=8.8), 7.92 (s, 1), 11.00 (s, 1). HRMS (FAB+) m/z: 590.2227 (MNa⁺ $C_{28}H_{33}N_5O_8Na$ requires 590.2220).

15

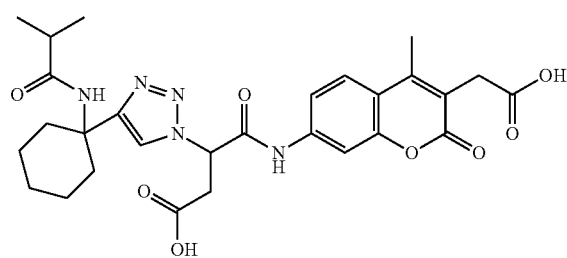

¹H NMR (400 MHz, DMSO d-6): δ 0.93-0.95 (d, 6, J=6.8) 1.23-1.25 (m, 1), 1.45-1.62 (m, 6), 1.72-1.74 (m, 2), 2.28-2.36 (m, 5), 3.23-3.41 (m, 2), 3.58 (s, 2), 5.68-5.72 (t, 1, J=7.4), 7.48-7.72 (d, 1, J=8.8), 7.60 (s, 1), 7.70 (s, 1), 7.79-7.81 (d, 1, J=8.8), 7.87 (s, 1), 11.02 (s, 1). HRMS (FAB+) m/z: 568.2407 (MH⁺ $C_{28}H_{34}N_5O_8$ requires 568.2407).

16

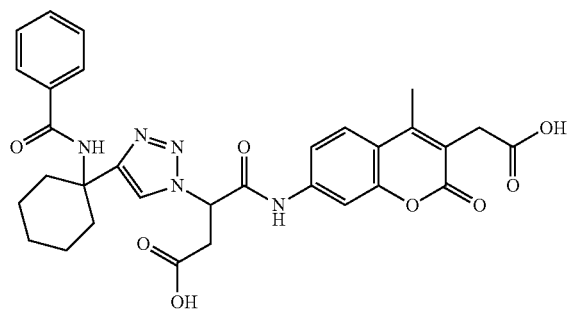

¹H NMR (400 MHz, DMSO d-6): δ 1.27-1.31 (m, 2), 1.51-1.56 (m, 6), 1.86-1.89 (m, 2), 2.36 (s, 3), 3.23-3.40 (m, 2), 3.58 (s, 2), 5.70-5.74 (t, 1, J=7.4), 7.41-7.44 (t, 2, J=7.2), 7.48-7.50 (d, 2, J=8.0), 7.70 (s, 1), 7.78-7.80 (d, 3, J=8.8), 8.04 (s, 1), 8.12 (s, 1), 11.00 (s, 1). HRMS (FAB+) m/z: 624.2070 (MNa⁺ $C_{31}H_{31}N_5O_8Na$ requires 624.2060).

17

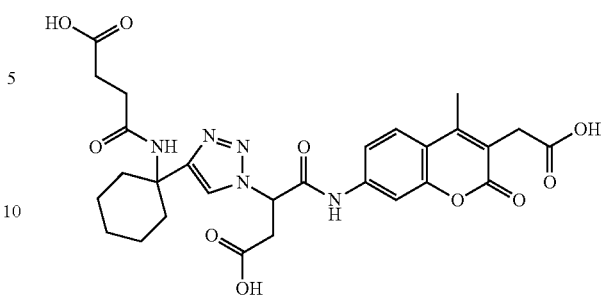

¹H NMR (400 MHz, DMSO d-6): δ 1.25-1.34 (m, 2), 1.44-1.53 (m, 8), 1.72-1.74 (m, 2), 2.28-2.30 (m, 2), 2.36 (s, 3), 3.20-3.39 (m, 2), 3.58 (s, 2), 5.67-5.71 (t, 1, J=7.4), 7.48-7.50 (d, 1, J=8.8), 7.71 (s, 1), 7.76 (s, 1), 7.79-7.81 (d, 1, J=8.8), 7.93 (s, 1), 10.99 (s, 1). HRMS (FAB+) m/z: 620.1969 (MNa⁺ $C_{28}H_{31}N_5O_{10}Na$ requires 620.1958).

18

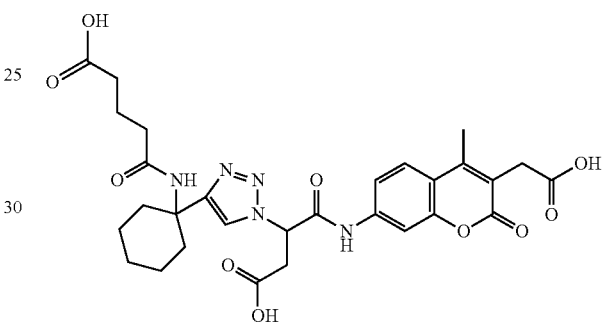

¹H NMR (400 MHz, DMSO d-6): 1.25-1.51 (m, 8), 1.65-1.69 (t, 2, J=7.2), 1.70-1.74 (m, 2), 2.12-2.15 (t, 2, J=7.2), 2.16-2.20 (m, 2), 2.36 (s, 3), 3.24-3.39 (m, 2), 3.58 (s, 2), 5.69-5.72 (t, 1, J=7.4), 7.48-7.50 (d, 1, J=8.8), 7.71 (s, 1), 7.73 (s, 1), 7.78-7.80 (d, 1, J=8.8), 7.95 (s, 1), 11.00 (s, 1). HRMS (FAB+) m/z: 634.2125 (MNa⁺ $C_{29}H_{33}N_5O_{10}Na$ requires 634.2120).

21

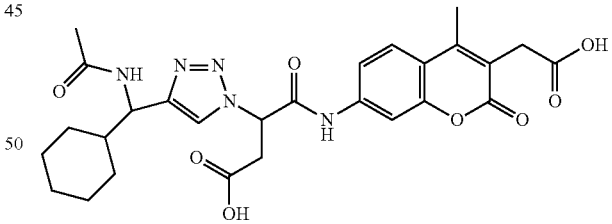

LRMS calculated for MH⁺ $C_{27}H_{31}N_5O_8$ 554.2. found 554.1.

22

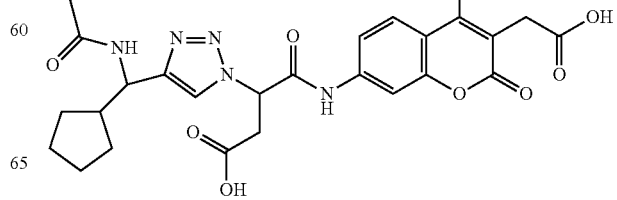

LRMS calculated for MH+ $C_{26}H_{29}N_5O_8$ 540.2. found 540.1.

23

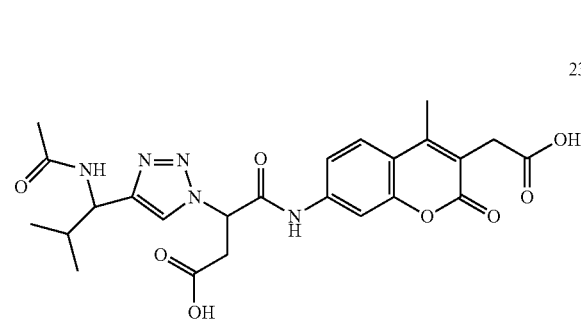 [SMILES: CC(=O)NC(c1cn(C(CC(=O)O)C(=O)Nc2ccc3c(C)c(CC(=O)O)c(=O)oc3c2)nn1)C(C)C]

LRMS calculated for MH+ $C_{24}H_{27}N_5O_8$ 514.2. found 514.1.

24

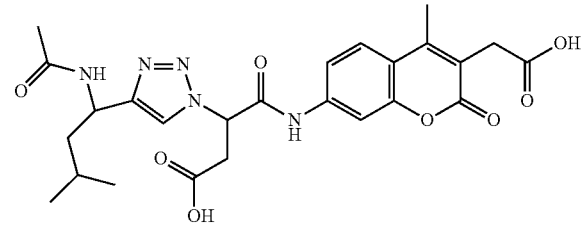

LRMS calculated for MH+ $C_{25}H_{29}N_5O_8$ 528.2. found 528.1.

25

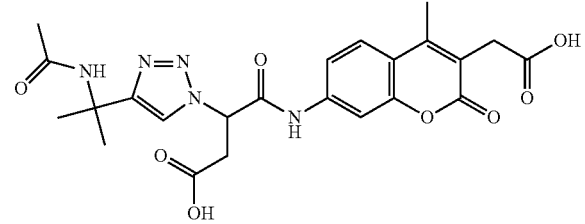

LRMS calculated for MH+ $C_{23}H_{25}N_5O_8$ 500.2. found 500.1.

26

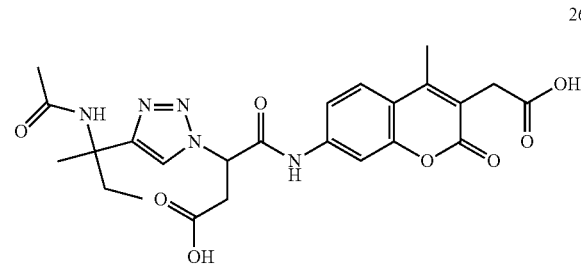 [SMILES: CC(=O)NC(C)(C)c1cn(C(CC(=O)O)C(=O)Nc2ccc3c(C)c(CC(=O)O)c(=O)oc3c2)nn1]

LRMS calculated for MH+ $C_{24}H_{27}N_5O_8$ 514.2. found 514.1.

27

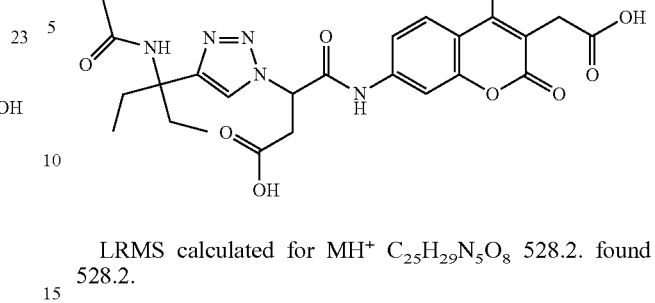

LRMS calculated for MH+ $C_{25}H_{29}N_5O_8$ 528.2. found 528.2.

28

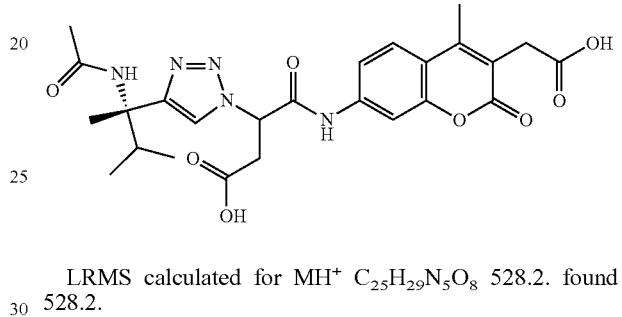

LRMS calculated for MH+ $C_{25}H_{29}N_5O_8$ 528.2. found 528.2.

29

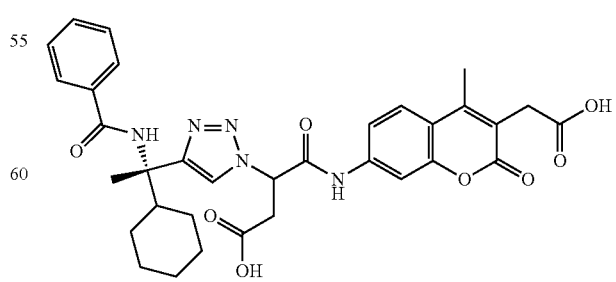

$^1$H NMR (400 MHz, DMSO d-6): δ 0.79-1.12 (m, 6) 1.32-1.35 (m, 2), 1.58 (s, 3), 1.67-1.70 (m, 2), 1.80 (s, 3), 2.01-2.03 (m, 1), 2.36 (s, 3), 3.21-3.46 (m, 2), 3.58 (s, 2), 5.70-5.73 (t, 1, J=7.4), 7.47-7.49 (d, 1, J=8.8), 7.66 (s, 1), 7.70 (s, 1), 7.79-7.81 (d, 1, J=8.8), 8.00 (s, 1), 10.99 (s, 1). HRMS (FAB+) m/z: 568.2407 (MH+ $C_{28}H_{34}N_5O_8$ requires 568.2415).

33

$^1$H NMR (400 MHz, DMSO d-6): δ 0.81-1.19 (m, 6) 1.57-1.60 (m, 2), 1.72 (s, 3), 1.78-1.81 (m, 2), 2.27-2.29 (m, 1), 2.36 (s, 3), 3.27-3.41 (m, 2), 3.58 (s, 2), 5.72-5.75 (t, 1, J=7.4), 7.43-7.50 (m, 4), 7.69 (s, 1), 7.73-7.75 (d, 2, J=8.0), 7.79-7.81 (d, 1, J=8.8), 8.04 (s, 1), 8.12 (s, 1), 11.00 (s, 1). HRMS (FAB+) m/z: 652.2383 (MNa⁺ $C_{33}H_{35}N_5O_8Na$ requires 652.2368).

7.20-7.22 (m, 4H), 7.40-7.43 (d, 1, J=7.2), 7.66-7.64 (d, 1, J=7.2), 7.72-7.74 (d, 1, J=8.8), 8.23 (s, 1), 10.89 (s, 1). HRMS (FAB+) m/z: 702.2210 (MNa⁺ $C_{33}H_{37}N_5O_9S$ requires 702.2202).

36

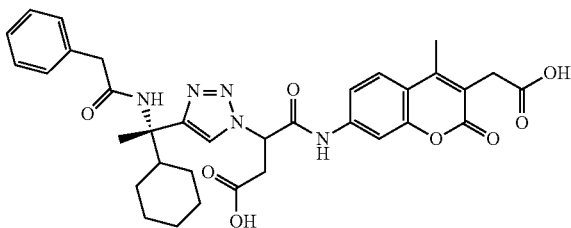

¹H NMR (400 MHz, DMSO d-6): δ 0.76-1.11 (m, 6) 1.30-1.33 (m, 2), 1.59 (s, 3), 1.65-1.70 (m, 4), 2.00-2.03 (m, 1), 2.37 (s, 3), 3.20-3.43 (m, 2), 3.58 (s, 2), 5.67-5.71 (t, 1, J=7.6), 7.17-7.27 (m, 5), 7.47-7.49 (d, 1, J=7.2), 7.71 (s, 1), 7.79-7.81 (d, 1, J=8.8), 7.84 (s, 1), 7.94 (s, 1), 11.00 (s, 1). HRMS (FAB+) m/z: 666.2540 (MNa⁺ $C_{34}H_{37}N_5O_8Na$ requires 666.2535).

37

¹H NMR (400 MHz, DMSO d-6): δ 0.94-1.15 (m, 8), 1.61 (s, 3), 1.77-1.87 (m, 2), 2.21-2.23 (m, 1), 2.36 (s, 3), 3.25-3.41 (m, 2), 3.58 (s, 2), 3.93 (s, 2), 5.87-5.91 (t, 1, J=7.6), 7.29-7.34 (m, 5), 7.48-7.50 (d, 1, J=8.8), 7.73 (s, 1), 7.80-7.82 (d, 1, J=8.8), 8.49 (s, 1), 10.99 (s, 1). HRMS (FAB+) m/z: 616.2771 (MH⁺ $C_{33}H_{38}N_5O_8$ requires 616.2764).

34

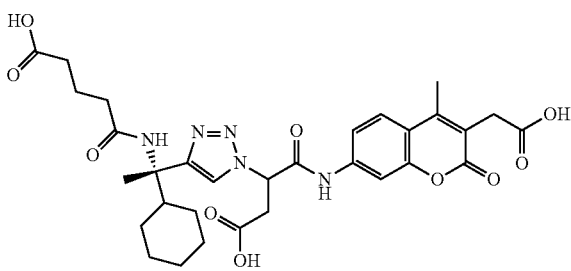

38

¹H NMR (400 MHz, DMSO d-6): δ 0.72-1.13 (m, 6) 1.32-1.36 (m, 2), 1.59 (s, 3), 1.61-1.67 (m, 4), 1.98-2.02 (m, 1), 2.10-2.17 (m, 4), 2.37 (s, 3), 3.26-3.43 (m, 2), 3.59 (s, 2), 5.70-5.74 (t, 1, J=7.4), 7.49-7.51 (d, 1, J=8.8), 7.60 (s, 1), 7.70 (s, 1), 7.80-7.82 (d, 1, J=8.8), 8.00 (s, 1), 11.00 (s, 1). HRMS (FAB+) m/z: 662.2438 (MNa⁺ $C_{31}H_{37}N_5O_{10}Na$ requires 662.2427).

¹H NMR (400 MHz, DMSO d-6): δ 0.96-0.99 (m, 4) 1.11-1.30 (m, 10), 1.62-1.65 (m, 2), 1.68 (s, 3), 1.73-1.77 (m, 1), 2.36 (s, 3), 3.05-3.19 (m, 4), 3.21-3.39 (m, 2), 3.58 (s, 2), 5.85-5.89 (t, 1, J=7.4), 7.46-7.48 (d, 1, J=8.8), 7.71 (s, 1), 7.79-7.81 (d, 1, J=8.8), 8.57 (s, 1), 11.00 (s, 1). HRMS (FAB+) m/z: 582.2928 (MH⁺ $C_{30}H_{40}N_5O_7$ requires 582.2932).

35

41

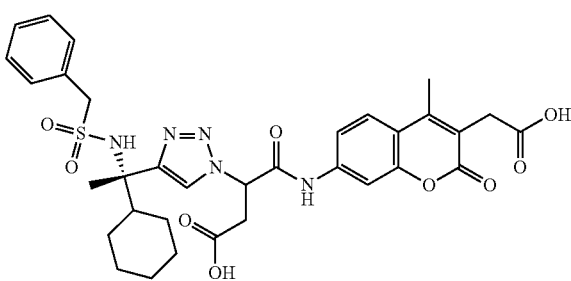

¹H NMR (400 MHz, DMSO d-6): δ 0.81-1.16 (m, 6) 1.54-1.57 (m, 5), 1.71-1.73 (m, 1), 1.91-1.94 (m, 1), 2.05-2.10 (m, 1), 2.34 (s, 3), 3.29-3.34 (m, 2), 3.42-3.46 (m, 1), 3.57 (s, 2), 3.63-3.67 (m, 1), 5.76-5.80 (t, 1, J=7.6), 7.12-7.14 (m, 2H),

¹H NMR (400 MHz, DMSO d-6): δ 0.78-1.13 (m, 6) 1.32-1.37 (m, 2), 1.60 (s, 3), 1.66-1.70 (m, 2), 2.01-2.06 (m, 1), 2.38 (s, 3), 3.22-3.42 (m, 4), 3.59 (s, 2), 3.71 (s, 3), 5.69-5.73 (t, 1, J=7.4), 6.74-6.82 (m, 3), 7.13-7.17 (t 1, J=7.6), 7.48-7.50 (d, 1, J=8.8), 7.72 (s, 1), 7.80 (s, 1), 7.82 (s, 1), 7.97 (s, 1), 11.00 (s, 1). HRMS (FAB+) m/z: 674.2826 (MH⁺ $C_{35}H_{40}N_5O_9Na$ requires 674.2819).

42

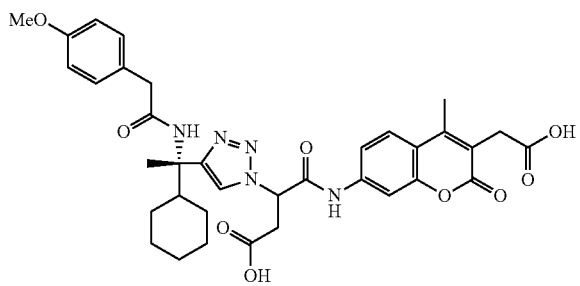

¹H NMR (400 MHz, DMSO d-6): δ 0.74-1.12 (m, 6) 1.34-1.37 (m, 2), 1.59 (s, 3), 1.62-1.67 (m, 2), 2.01-2.06 (m, 1), 2.37 (s, 3), 3.19-3.45 (m, 4), 3.59 (s, 2), 3.69 (s, 3), 5.70-5.74 (t, 1, J=7.4), 6.80-6.83 (d, 2, J=8.4), 7.12-7.14 (d, 2, J=8.4), 7.48-7.50 (d, 1, J=8.8), 7.72 (s, 1), 7.76 (s, 1), 7.79-7.82 (d, 1, J=8.8), 7.95 (s, 1), 11.00 (s, 1). HRMS (FAB+) m/z: 674.2826 (MH+ $C_{35}H_{40}N_5O_9Na$ requires 674.2828).

45

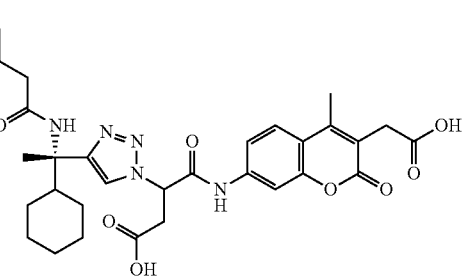

¹H NMR (400 MHz, DMSO d-6): δ 0.77-1.12 (m, 6) 1.33-1.37 (m, 1), 1.60 (s, 3), 1.65-1.69 (m, 2), 2.02-2.06 (m, 2), 2.37 (s, 3), 3.19-3.47 (m, 4), 3.59 (s, 2), 5.70-5.74 (t, 1, J=7.4), 7.47-7.55 (m, 4), 7.61 (s, 1), 7.71 (s, 1), 7.79-7.82 (d, 1, J=8.8), 7.97 (s, 1), 8.00 (s, 1), 11.00 (s, 1). HRMS (FAB+) m/z: 712.2594 (MH+ $C_{35}H_{37}N_5O_8$ requires 712.2590).

46

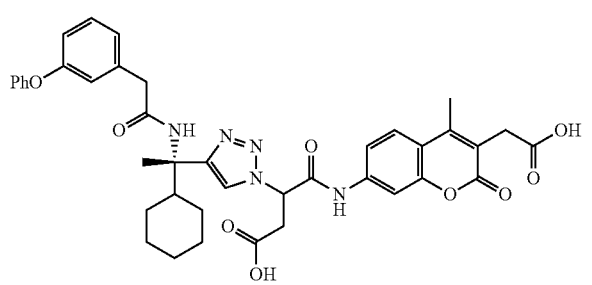

¹H NMR (400 MHz, DMSO d-6): δ 0.75-1.10 (m, 6) 1.30-1.35 (m, 2), 1.57 (s, 3), 1.61-1.66 (m, 2), 2.00-2.05 (m, 1), 2.37 (s, 3), 3.23-3.46 (m, 4), 3.59 (s, 2), 5.72-5.77 (t, 1, J=7.4), 6.84-6.86 (m, 2), 6.92 (s, 1), 6.97-6.99 (d, 2, J=7.6), 7.11-7.13 (m, 1), 7.27-7.30 (t, 1, J=7.6), 7.34-7.38 (t, 2, J=7.6), 7.48-7.50 (d, 1, J=8.8), 7.71 (s, 1), 7.79-7.81 (d, 2, J=8.8), 7.96 (s, 1), 11.00 (s, 1). HRMS (FAB+) m/z: 758.2802 (MNa+ $C_{40}H_{41}N_5O_9Na$ requires 758.2810).

40

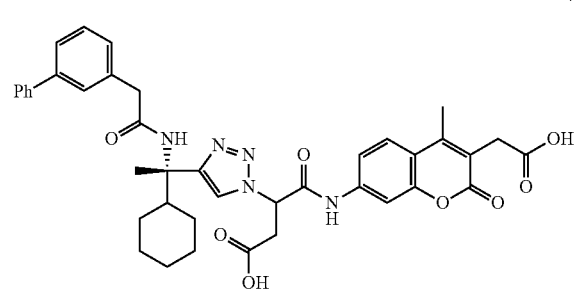

¹H NMR (400 MHz, DMSO d-6): δ 0.72-1.11 (m, 6) 1.34-1.37 (m, 2), 1.56 (s, 3), 1.58-1.61 (m, 2), 2.03-2.08 (m, 1), 2.37 (s, 3), 3.23-3.52 (m, 4), 3.59 (s, 2), 5.70-5.74 (t, 1, J=7.4), 7.21-7.22 (d, 1, J=7.2), 7.34-7.36 (m, 2), 7.43-7.49 (m, 3), 7.55 (s, 1), 7.60-7.62 (d, 2, J=7.2), 7.71 (s, 1), 7.78-7.81 (d, 1, J=8.8), 7.91 (s, 1), 7.99 (s, 1), 10.99 (s, 1). HRMS (FAB+) m/z: 720.3033 (MH+ $C_{40}H_{42}N_5O_8$ requires 720.3044).

II. Synthesis of Aryloxy-Methyl Ketones and Intermediates

Figure 6:
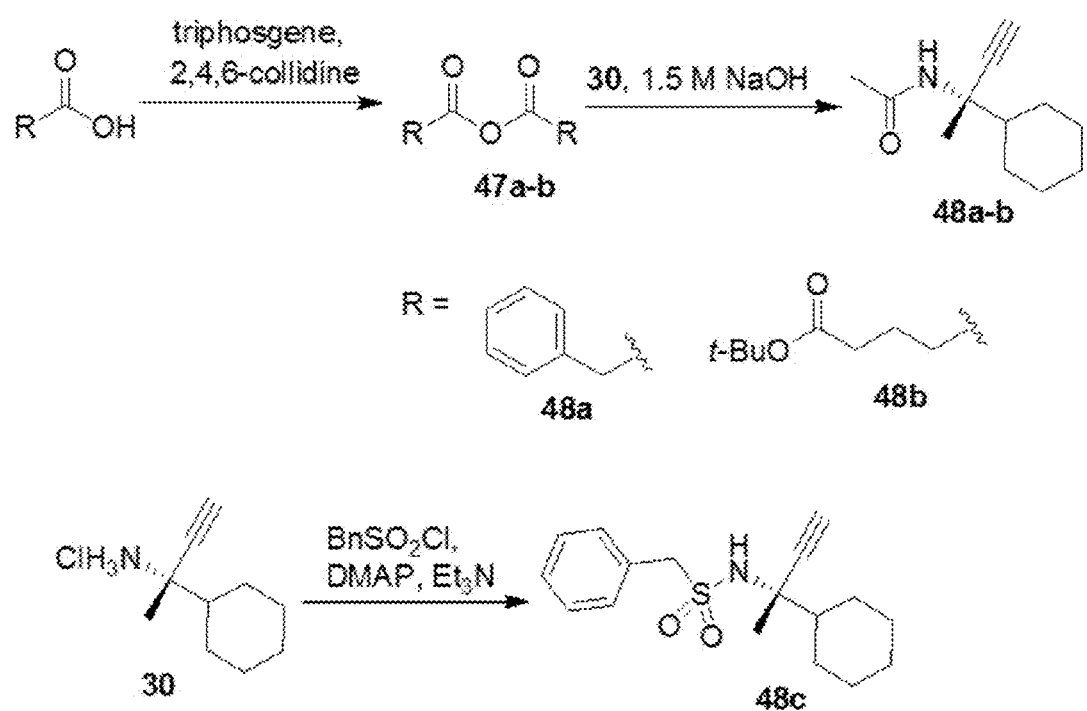
FIG. 6 illustrates a synthesis scheme for the general synthesis of propargyl amide intermediates.

A general scheme for the synthesis of propargyl amide intermediates is shown in FIG. 6.

General Synthesis of Propargyl Amide Intermediates.

General Synthesis of Symmetric Anhydrides 47a-b in Scheme 6 (Procedure A).

Triphosgene (1 equiv) was dissolved in THF in a flame dried round-bottom flask and placed under nitrogen. The solution was stirred and cooled in an ice-water bath. The carboxylic acid (5 equiv) was added to the above solution. After the acid dissolved, 2,4,6-collidine (10 equiv) was added slowly. The round-bottom flask was removed from the ice-water bath and the reaction mixture was stirred at rt for 15 min. The reaction mixture was transferred to a separatory funnel and EtOAc (250 mL) was added. The organic layer was washed with water (120 mL), 1.0M aqueous hydrochloric acid solution (120 mL×2), water (120 mL), 1.0M aqueous sodium hydroxide solution (120 mL×2), and water (120 mL×2). The organic layer was dried over anhydrous sodium

43

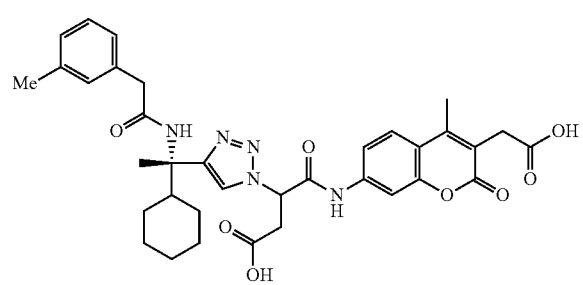

¹H NMR (400 MHz, DMSO d-6): δ 0.75-1.13 (m, 6) 1.34-1.37 (m, 2), 1.60 (s, 3), 1.67-1.69 (m, 2), 2.02-2.07 (m, 1), 2.25 (s, 3), 2.37 (s, 3), 3.23-3.42 (m, 4), 3.59 (s, 2), 5.68-5.72 (t, 1, J=7.4), 6.98-7.03 (m, 3), 7.12-7.16 (t, 1, J=7.6), 7.47-7.50 (d, 1, J=8.8), 7.72 (s, 1), 7.79 (s, 1), 7.81 (s, 1), 7.96 (s, 1), 11.01 (s, 1). HRMS (FAB+) m/z: 680.2696 (MNa+ $C_{35}H_{39}N_5O_8Na$ requires 680.2710).

sulfate, filtered, and concentrated under reduced pressure to obtain the desired product.

5-(tert-butoxy)-5-oxopentanoic Anhydride (47b).

Procedure A was used to prepare 5-(tert-butoxy)-5-oxopentanoic anhydride (1.61 g, 76%) from 5-tert-butoxy-5-pentanoic acid (1.88 g, 10.0 mmol), which was prepared from glutaric anhydride according to a previous literature procedure (Lelais et al. (2004) *Helv. Chim. Acta*, 87:1545-1560), triphosgene (0.590 g, 2.00 mmol), and 2,4,6-collidine (2.64 mL, 20.0 mmol). $^1$H NMR (400 MHz, CDCl$_3$, δ): 1.41 (s, 18H), 1.88-1.92 (t, 4H, J=7.2 Hz), 2.26-2.30 (t, 4H, J=7.2 Hz), 2.47-2.51 (t, 4H, J=7.2 Hz). $^{13}$C NMR (100 MHz, CDCl$_3$, δ): 19.7, 28.3, 34.2, 34.4, 80.8, 169.0, 172.2. HRMS-FAB (m/z): [M+Na]$^+$ calcd for C$_{18}$H$_{30}$O$_7$Na, 381.1889. found, 381.1882.

Phenylacetic Acid Anhydride (47a).

Procedure A was used to prepare phenylacetic acid anhydride (1.34 g, 88%) from phenylacetic acid (1.36 g, 10.0 mmol), triphosgene (0.59 g, 2.00 mmol), and 2,4,6-collidine (2.64 mL, 20.0 mmol). $^1$H NMR (400 MHz, CDCl$_3$): δ 3.74 (s, 4), 7.22-7.27 (m, 4), 7.31-7.35 (m, 6). $^{13}$C NMR (100 MHz, CDCl$_3$): δ 42.2, 127.8, 129.0, 129.6, 132.1, 167.1. HRMS (FAB+) m/z: 255.1021 (MH$^+$ C$_{16}$H$_{15}$O$_3$ requires 255.1026).

General Synthesis of Propargyl Amides 48a-b (Procedure B).

A 1.50 M sodium hydroxide solution was added to the hydrochloride salt of (S)-2-amino-2-cyclohexyl-3-butyne 30 (1 equiv). A solution of anhydride (0.17 M, 1 equiv) in chloroform was added to the above solution and heated at reflux for 24 h. The reaction mixture was transferred to a reparatory funnel, and EtOAc (150 mL) and water (15 mL) were added. The organic layer was washed with brine (25 mL), 10 M aqueous sodium hydroxide solution (25 mL×4), brine (25 mL×4), and water (25 mL×2). The organic layer was dried over anhydrous sodium sulfate, filtered, and concentrated under reduced pressure. The product was purified by flash chromatography (1:1 hexanes:EtOAc) to afford the desired product.

Propargyl Amide 48a.

Amide 48a (0.100 g, 71%) was prepared 0.099 g (0.530 mmol) of hydrochloride salt of (S)-2-amino-2-cyclohexyl-3-butyne 30 and phenylacetic acid anhydride (0.17M, 0.102 g, 0.530 mmol, 1 equiv) in chloroform (3.10 mL) using Procedure B. $^1$H NMR (400 MHz, CDCl$_3$): δ 0.95-1.05 (m, 4), 1.06-1.09 (m, 2), 1.57 (s, 3), 1.62-1.74 (m, 5), 1.90-2.05 (t, 2, J=12.0), 2.31 (s, 1), 3.54 (s, 2), 5.43 (br s, 1), 7.25-7.31 (dd, 3, J=7.6, 7.2), 7.35-7.38 (m, 2). $^{13}$C NMR (100 MHz, CDCl$_3$): δ 24.4, 26.3, 27.5, 27.7, 44.4, 44.8, 55.7, 71.5, 85.4, 127.5, 129.2, 129.5, 135.2, 169.8. HRMS (FAB+) m/z: 270.1858 (MH$^+$ C$_{18}$H$_{24}$NO requires 270.1853).

Propargyl Amide 48b. Amide 48b (0.41 g, 70%) was prepared from 0.34 g (1.80 mmol) of hydrochloride salt of (S)-2-amino-2-cyclohexyl-3-butyne 30 and 5-(tert-butoxy)-5-oxopentanoic anhydride (0.17 M, 1.80 mmol, 1 equiv) in chloroform (10.6 mL) using Procedure B. $^1$H NMR (400 MHz, CDCl$_3$, δ): 1.16-1.25 (m, 6H), 1.42 (s, 9H), 1.52 (s, 3H), 1.67-1.76 (m, 5H), 1.87-1.91 (t, 2H, J=7.2), 2.15-2.19 (t, 2H, J=7.2), 2.23-2.27 (t, 2H, J=7.2), 2.32 (s, 1H). $^{13}$C NMR (100 MHz, CDCl$_3$, δ): 21.3, 24.5, 25.4, 26.4, 27.7, 27.9, 28.3, 34.6, 36.4, 44.2, 55.9, 71.5, 80.6, 171.3, 172.9. HRMS-FAB (m/z): [M+Na]$^+$ calcd for C$_{19}$H$_{31}$NO$_3$Na, 344.2202. found, 344.2197.

Propargyl Sulfonamide 48c.

To a flame-dried tube was added the hydrochloride salt of (S)-2-amino-2-cyclohexyl-3-butyne 30 (0.20M, 0.25 g, 1.32 mmol, 1 equiv), phenylmethanesulfonyl chloride (0.27 g, 1.45 mmol, 1.10 equiv), and DMAP (0.031 g, 0.26 mmol, 0.2 equiv) in CH$_2$Cl$_2$ (6.6 mL) and the resulting mixture was stirred. To the solution was added NEt$_3$ (0.40 mL, 2.9 mmol, 2.2 equiv), and the mixture was then stirred in a sealed tube, which was heated in a 60° C. oil bath for 18 h. The reaction mixture was transferred to a reparatory funnel, and aqueous NH$_4$Cl (10 mL) was added followed by extraction with CH$_2$Cl$_2$ (30 mL×3). The organic layer was dried over anhydrous sodium sulfate, filtered, and concentrated under reduced pressure. The product was purified by flash chromatography (7:3 hexanes:EtOAc) to afford the desired product as an orange solid (0.235 g, 59%). $^1$H NMR (400 MHz, CDCl$_3$, δ): 1.00-1.12 (m, 5H), 1.53 (s, 3H), 1.58-1.61 (m, 2H), 1.76-1.87 (m, 2H), 1.89-2.02 (m, 2H), 2.63 (s, 1H), 4.14 (s, 1H), 4.48 (s, 2H), 7.34-7.35 (m, 3H), 7.43-7.44 (d, 2H, J=4.8). $^{13}$C NMR (100 MHz, CDCl$_3$, δ): 26.1, 26.3, 27.0, 28.0, 48.4, 57.4, 60.1, 74.3, 84.6, 128.8, 129.9, 131.3. HRMS-FAB (m/z): [M+H]$^+$ calcd for C$_{17}$H$_{23}$NO$_2$S, 305.1450. found, 305.1457.

General Synthesis of Azido-Aryloxy Methyl Ketone.

Figure 7:
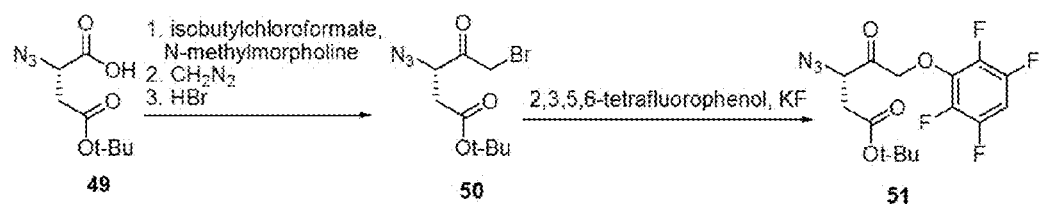
FIG. 7 illustrates a general synthesis scheme for azido-aryloxy methyl ketones.

A scheme for the synthesis of azido-aryloxy methyl ketones is shown in FIG. 7.

Bromomethyl Ketone 50.

The method was adapted from a previous literature procedure (Chino et al. (2002) *Tetrahedron*, 58: 6305-6310.). Azido acid 49 was prepared from Asp(Ot-Bu)-OH according to a previously reported literature procedure (Lundquist and Pelletier (2001) *Org. Lett.*, 3: 781-783). To a 0.1M solution of azido acid 49 (1.00 g, 4.65 mmol) and N-methylmorpholine (0.56 mL, 5.12 mmol) in THF (46.5 mL) at −78° C. was added isobutylchloroformate (0.66 mL, 5.12 mmol). The reaction mixture was stirred for 15 min and the resulting heterogenous mixture was canula filtered into a flask at −78° C. Diazomethane, prepared from Diazald (3.01 g, 14.14 mmol), was bubbled slowly while the reaction mixture was maintained at −78° C. After addition of diazomethane was complete, the reaction flask was stoppered and kept in the refrigerator at −4° C. overnight. The reaction mixture was then treated with 40% aqueous HBr (0.953 mL) and stirred for 15 min at 0° C. The reaction mixture was diluted with EtOAc (50 mL) and washed with 10 wt % aqueous citric acid (2×10 mL), saturated aqueous NaHCO$_3$ (2×10 mL), and aqueous saturated NaCl (10 mL). The organic layer was dried with Na$_2$SO$_4$, filtered, and concentrated under reduced pressure to afford 50 as a yellow oil (81%). The crude material was used for the subsequent reaction. $^1$H NMR (400 MHz, CDCl$_3$): δ 1.45 (s, 9), 2.74-2.94 (m, 2), 4.09-4.27 (m, 2), 4.48-4.51 (t, 1, J=6.0). $^{13}$C NMR (100 MHz, CDCl$_3$): δ 28.2, 32.4, 37.6, 62.1, 82.6, 169.0, 198.2. HRMS (FAB+) m/z: 298.0379 (MLi$^+$ C$_9$H$_{14}$N$_3$O$_3$Li requires 298.0383).

Azido-Aryloxy Methyl Ketone 51.

A solution of 2,3,4,6-tetrafluorophenol (0.45 g, 0.57 M, 2.73 mmol, 3.2 equiv) and potassium fluoride (0.22 g, 8.73 mmol, 3.2 equiv) in DMF was added to a flame-dried reaction vessel under nitrogen. The reaction mixture was cooled to 0° C. in an ice-water bath and (S)-tert-butyl-3-azido-5-bromo-4-oxopentanoate 50 (0.80 g, 2.73 mmol, 1 equiv) was added dropwise. After stirring at 0° C. for 1.5 h, the mixture was diluted with diethyl ether (125 mL) and transferred to a separatory funnel. The organic layer was washed with aqueous sodium bicarbonate (75 mL×2) and brine (75 mL). The organic layer was dried over anhydrous sodium sulfate, filtered, and concentrated under reduced pressure. The product was purified by flash chromatography (7:3 hexanes:EtOAc) to afford the desired product 51 as a pale yellow oil (0.560 g, 55%). $^1$H NMR (400 MHz, CDCl$_3$): δ 1.41 (s, 9), 2.75-2.81

(m, 2), 4.41-4.45 (t, 1, J=5.6), 5.18 (s, 2), 6.74-6.80 (m, 1). HRMS (FAB+) m/z: 400.0896 (MNa+ $C_{15}H_{15}N_3O_4F_4Na$ requires 400.0893).

General Synthesis of Aryloxy Methyl Ketone Inhibitors.

Figure 8:
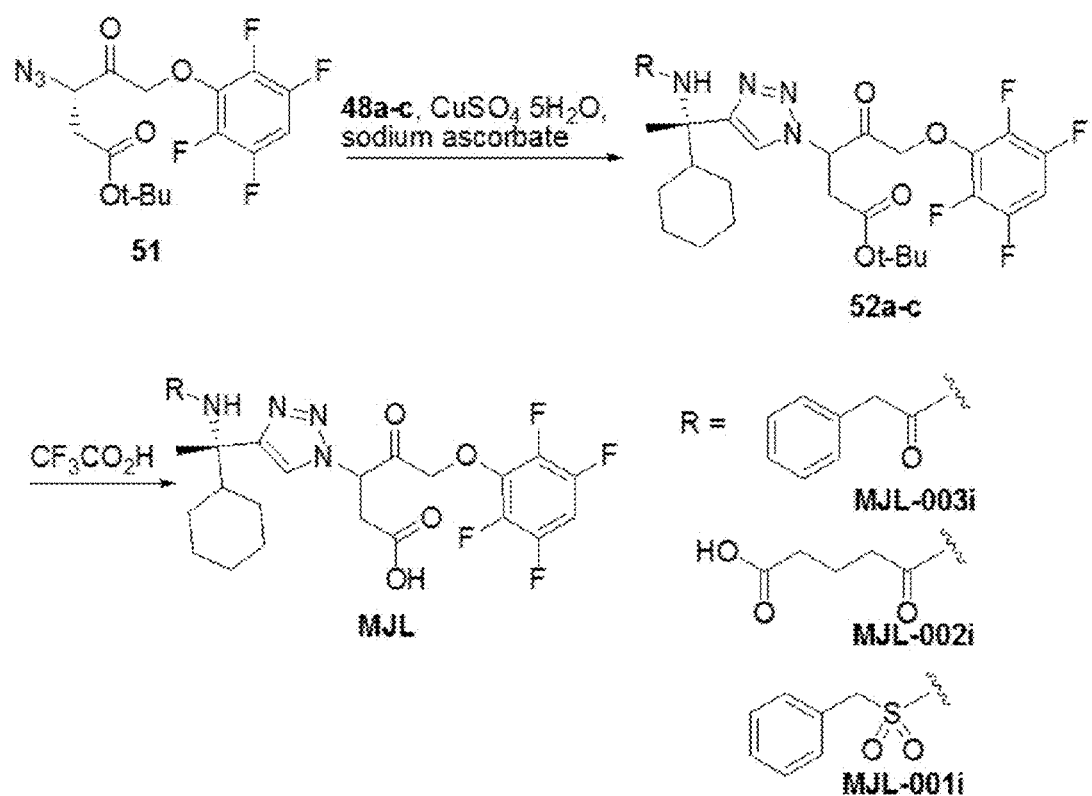
FIG. 8 illustrates a scheme for the general synthesis of aryloxy methyl ketone inhibitors.

General Procedure for Copper(I)-Catalyzed Synthesis of 1,4-Disubstituted 1,2,3-Triazoles 52a-c in Scheme 7 (FIG. 8) (Procedure C).

The following procedure was adapted from a previous literature procedure (Rostovtsev et al. (2002) Angew. Chem. Int. Ed., 41: 2596-2599). To a solution of azido-aryloxy methyl ketone 51 (0.25 M, 1 equiv) and propargyl amide 48a-c (1 equiv) in 1:1 water/tert-butanol was added sodium ascorbate (1 equiv of freshly prepared 1.0 M aqueous solution). A solution of copper(II) sulfate pentahydrate (0.10 equiv of a freshly prepared 0.3M aqueous solution) was added to the reaction mixture and was vigorously stirred overnight. The reaction mixture was diluted with 10 mL of water and was extracted with EtOAc (3×10 mL). The organic layer was washed with brine (15 mL) and dried over sodium sulfate, filtered, and concentrated under reduced pressure. The product was purified by flash chromatography (7:3 hexanes:ethyl acetate) to afford the desired product.

Aryloxy Methyl Ketone-Ester 52a.

Procedure C was followed using azido-aryloxy methyl ketone 6 (0.11 g, 0.300 mmol), propargyl amide 48a (0.08 g, 0.300 mmol), 1.0 M sodium ascorbate (0.30 mL, 0.300 mmol), and 0.3 M copper(II) sulfate pentahydrate (0.10 mL, 0.03 mmol). After chromatography the product was obtained as a pale yellow solid (0.095 g, 49%). $^1$H NMR (400 MHz, CDCl$_3$, δ): 0.62-0.86 (m, 3H), 1.10-1.19 (m, 2H), 1.41 (s, 9H), 1.50-1.66 (m, 4H), 1.71 (s, 3H), 2.14-2.2 (t, 1H, J=12.0), 3.03-3.37 (m, 2H), 3.52 (s, 2H), 4.85-4.92 (m, 2H), 5.80-5.84 (t, 1H, J=7.2), 6.26 (s, 1), 6.77-6.82 (m, 1H), 7.26-7.30 (m, 3H), 7.34-7.38 (m, 2H), 7.53 (s, 1H). HRMS (FAB+) m/z: 647.2857 (MNa+ $C_{33}H_{39}N_4O_5F_4$ requires 647.2858).

Aryloxy Methyl Ketone-Ester 52b.

Procedure C was followed using azido-aryloxy methyl ketone 6 (0.15 g, 0.400 mmol), propargyl amide 48b (0.13 g, 0.400 mmol), 1.0 M sodium ascorbate (0.40 mL, 0.400 mmol), and 0.3 M copper(II) sulfate pentahydrate (0.13 mL, 0.04 mmol). After chromatography the product was obtained as a pale yellow solid (0.165 g, 60%). $^1$H NMR (400 MHz, CDCl$_3$, δ): 0.75-0.96 (m, 3H), 1.13-1.25 (m, 3H), 1.38 (s, 9H), 1.41 (s, 9H), 1.56-1.64 (m, 5H), 1.71 (s, 3H), 1.82-1.87 (t, 2H, J=7.2), 2.18-2.24 (m, 4H), 3.07-3.61 (m, 2H), 4.89 (s, 2H), 5.81-5.86 (dd, 1H, J=7.2, 13.6), 6.51 (s, 1H), 6.75-6.79 (m, 1H), 7.59 (s, 1H). HRMS (FAB+) m/z: 721.3193 (MNa+ $C_{34}H_{46}N_4O_7F_4NA$ requires 721.3200.

Aryloxy Methyl Ketone-Ester 52c.

Procedure C was followed using azido-aryloxy methyl ketone 6 (0.07 g, 0.200 mmol), propargyl sulfonamide 48c (0.06 g, 0.200 mmol), 1.0 M sodium ascorbate (0.02 mL, 0.200 mmol), and 0.3 M copper(II) sulfate pentahydrate (0.07 mL, 0.02 mmol). After chromatography the product was obtained as a pale yellow solid (0.09 g, 65%). $^1$H NMR (400 MHz, CDCl$_3$, δ): 0.86-1.14 (m, 6H), 1.48 (s, 9H), 1.74 (s, 3H), 1.75-1.88 (m, 3H), 1.91-1.98 (m, 2H), 3.10-3.16 (m, 2H, J=7.2, 17.2), 3.87-4.05 (m, 2H), 4.78 (s, 1H), 4.87-4.92 (m, 2H), 5.87-5.90 (t, 1H, J=6.8), 6.71-6.79 (m, 1H), 7.30-7.33 (m, 5H), 7.62 (s, 1H). HRMS (FAB+) m/z: 705.2351 (MNaC$_{32}$H$_{38}$N$_4$O$_6$F$_4$SNa requires 705.2346).

General Procedure for Deprotection of Tert-Butyl Esters (Procedure D).

To a 0.33 M solution of aryloxy methyl ketone-ester in CH$_2$Cl$_2$ was added a solution of 95% trifluoroacetic acid (TFA):2.5% H$_2$O:2.5% triisopropylsilane. The reaction mixture was stirred for 1 h at rt. The crude reaction mixture was purified by HPLC [preparatory reverse phase C$_{18}$ column (24.1×250 mm), CH$_3$CN/H$_2$O-0.1% TFA, 5:95 to 95:5 over 55 min; 10 mL/min, 254 nm detection] and lyophilized to afford the pure product.

Aryloxy Methyl Ketone Inhibitor MJL-003i.

Procedure D was followed using aryloxy methyl ketone-ester 52a (0.096 g, 0.150 mmol) and 95% TFA:2.5% H$_2$O: 2.5% triisopropylsilane (1.05 mL) in CH$_2$Cl$_2$ (0.45 mL) to afford inhibitor MJL-003i as a white solid (0.030 g, 32%). $^1$H NMR (400 MHz, DMSO-d$_6$, δ): 0.76-1.16 (m, 8H), 1.59 (s, 3H), 1.66-1.70 (m, 2H), 2.01-2.05 (m, 1H), 3.19-3.49 (m, 4H), 4.89-4.93 (d, 1H, J=18.0), 5.17-5.23 (dd, 1H, J=6.4, 18.0), 5.86-5.90 (t, 1H, J=8.0), 7.17-7.27 (m, 5H), 7.53-7.59 (m, 1H), 7.96 (s, 1H), 8.18 (s, 1H). HRMS (FAB+) m/z: 591.2231 (MH+ $C_{29}H_{31}N_4O_5F_4$ requires 591.2239).

Aryloxy Methyl Ketone Inhibitor MJL-002i.

Procedure D was followed using aryloxy methyl ketone-ester 52b (0.70 g, 0.100 mmol) and 95% TFA:2.5% H$_2$O: 2.5% triisopropylsilane (1.00 mL) in CH$_2$Cl$_2$ (0.43 mL) to afford inhibitor MJL-002i as a white solid (0.050 g, 58%). $^1$H NMR (400 MHz, CD$_3$OD, δ): 0.70-1.15 (m, 8H), 1.31-1.50 (m, 2H), 1.53 (s, 3H), 1.56-1.58 (m, 2H), 1.67-1.72 (m, 1H), 1.87-1.94 (m, 2H), 2.08-2.13 (dd, 2H, J=7.2, 14.4), 2.16-2.22 (dd, 2H, J=7.2, 14.4), 3.09-3.19 (m, 2H), 4.06-4.21 (m, 2H), 5.34-5.37 (t, 1H, J=5.2), 7.01-7.05 (m, 1H), 7.69 (s, 1H). HRMS (FAB+) m/z: 609.1946 (MNa+ $C_{26}H_{30}N_4O_7F_4Na$ requires 609.1948.

Aryloxy Methyl Ketone Inhibitor MJL-001i.

Procedure D was followed using aryloxy methyl ketone-ester 52c (0.06 g, 0.100 mmol) and 95% TFA:2.5% H$_2$O: 2.5% triisopropylsilane (0.70 mL) in CH$_2$Cl$_2$ (0.30 mL) to afford inhibitor MJL-001i as a white solid (0.030 g, 49%). $^1$H NMR (400 MHz, DMSO-d$_6$, δ): 0.83-1.16 (m, 8H), 1.52 (s, 3H), 1.72-1.75 (m, 1H), 1.91-2.00 (m, 2H), 3.26-3.31 (m, 2H), 3.62-3.82 (m, 2H), 4.89-4.93 (d, 1H, J=18.0), 5.17-5.23 (dd, 1H, J=6.4, 18.0), 5.96-5.98 (m, 1H), 7.24-7.28 (m, 5H), 7.56-7.76 (m, 1H), 8.09 (s, 1H). HRMS (FAB+) m/z: 649.1724 (MNa+ $C_{28}H_{30}N_4O_6F_4Na$ requires 649.1720.

III. AMCA Substrate and Irreversible Inhibitor Assays.

General Procedure for Assays.

Caspases-3, -6, -7, -8, and -9 were provided by Guy Salvesen's laboratory at the Burnham Institute (La Jolla, Calif.). Caspase-1 was purchased from EMD Biosciences (San Diego, Calif.) and Caspase-2 was purchased from Biomol International (Plymouth Meeting, Pa.). Caspase substrates Ac-DEVD-AMC, Ac-VDVAD-AFC, and Ac-LEHD-AFC were purchased from EMD Biosciences (San Diego, Calif.) and Ac-VDVAD-AMC was purchased from Biomol International (Plymouth Meeting, Pa.). The proteolytic cleavage of N-acyl aminocoumarins by caspases was conducted in Dynatech Microfluor fluorescence 96-well microtiter plates, and readings were taken on a Molecular Devices Spectra Max Gemini XS instrument. The excitation wavelength was 370 nm and the emission wavelength was 455 nm for AMCA substrates, the excitation wavelength was 355 nm and the emission wavelength was 450 nm for peptidyl AMC substrates, and the excitation wavelength was 430 nm and the emission wavelength was 535 nm for peptidyl AFC substrates.

Assay Procedure for AMCA Substrates.

Figure 10:
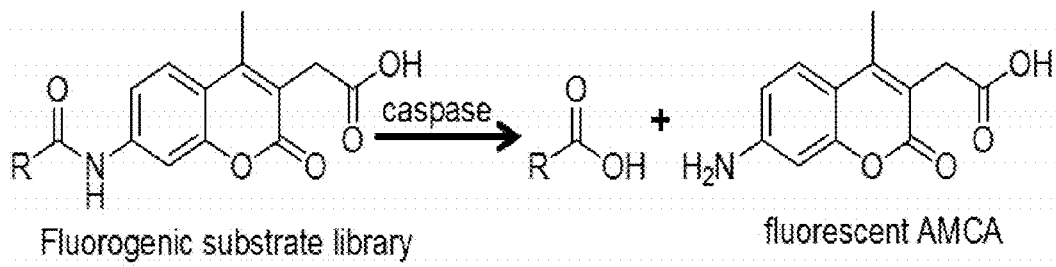
FIG. 10 illustrates a general scheme for AMCA substrate screening. A general substrate is shown that is proteolytically cleaved by a caspase to give the carboxylic acid (RCOOH) and the fluorescent AMCA product. This method monitors cleavage efficiency of the substrate against caspase. The fluorescence observed relates to cleavage efficiency. If the R group is not optimal for processing by caspase, no fluorescence is observed.

FIG. 10 shows a general substrate that is proteolytically cleaved by caspase to give the carboxylic acid (RCOOH) and the fluorescent AMCA product. This method monitors cleavage efficiency of the substrate against caspase. The fluorescence observed relates to cleavage efficiency. If the R group is not optimal for processing by caspase, no fluorescence is observed.

Assays were conducted at 37° C. in duplicate with and without the enzyme according to previously reported protocols (Wood et al. (2005) *J. Am. Chem. Soc.*, 127: 15521-15527). In each well was placed 38 µL of enzyme solution and 2 µL of a DMSO substrate solution. Relative fluorescent units (RFU) were measured at regular intervals over a period of time (maximum 15 min). A plot of RFU versus time was made for each substrate with and without caspase-3 or caspase-6. The slope of the plotted line gave relative $k_{cat}/K_m$ of each substrate for caspase-3 or caspase-6.

Assay Procedure for Irreversible Inhibitors.

The $H_{inact}/K_i$ for inhibitors were determined under pseudo-first order conditions using the progress curve method (Eckici et al. (2006) *J. Med. Chem.*, 49: 5728-5749; Bieth (1995) *Meth. Enzymol.*, 248: 59-84). Assay wells contained a mixture of inhibitor and AMC or AFC substrate in buffer. Aliquots of caspase were added to each well to initiate the assay. Hydrolysis of the AMC or AFC substrate was monitored fluorometrically for 45 min. To determine the inhibition parameters, time points for which the control ([I]=0) was linear were used. For each inhibitor, a $k_{obs}$ was calculated for at least four different concentrations of inhibitors via a non-linear regression of the data according to the equation $P=(v_i/k_{obs})[1-\exp(-k_{obs}t)]$ (where product formation=P, initial rate=$v_i$, time=t, and the first-order rate constant=$k_{obs}$). If $k_{obs}$ varied linearly with [I], then the association constant kass was determined by linear regression analysis using $k_{obs}=(k_{ass}[I])/(1+[S]/K_m)$ where [S] is the concentration of the substrate. If $k_{obs}$ varied hyperbolically with [I], then non-linear regression analysis was performed to determine $k_{inact}/K_i$ using $k_{obs}=k_{inact}[I]/([I]+K_i*(1+[S]/K_m))$. Inhibition was measured in duplicate and the average of is reported.

Caspase-1.

Caspase-1 kinetic assays were performed using Ac-WEHD-AMC ($K_m$=4.0 µM) as the substrate. The assay buffer was 100 mM HEPES, 20% (w/v) glycerol, 10% (w/v) sucrose, 0.1% (w/v) CHAPS, and 10 mM DTT solution in $H_2O$ at pH 7.5. The concentration of the enzyme stock solution was 20 nM in the assay buffer. The concentrations of inhibitor stock solutions in DMSO ranged from ($5.00\times10^{-7}$ to $1.12\times10^{-4}$). The concentration of the substrate stock solution was 80 µM in assay buffer. The reaction was started by adding 140 µL of assay buffer, 10 µL of various amounts of inhibitor (final concentrations ranging from $2.50\times10^{-8}$ M to $5.60\times10^{-6}$ M), 10 µL of substrate (final concentration 4.0 µM). Then 40 µL of Caspase-1 (final concentration of 4 nM) was added to the mixture after incubating for 5 min at 37° C.

Caspase-2.

Caspase-2 kinetic assays were performed using Ac-VDVAD-AMC ($K_m$=80.2 µM) as the substrate and with the same conditions as described for Caspase-1 using the following modifications: The assay buffer was 20 mM Pipes, 200 mM NaCl, 0.2% (w/v) CHAPS, 20% (w/v) sucrose, 20 mM DTT, and 2 mM EDTA solution in $H_2O$ at pH 7.2. The concentration of the substrate stock solution was 1.60 mM in assay buffer (final concentration: 80.2 µM). The inhibitor stock solutions ranged from 0.02 M to $3.12\times10^{-5}$ M in DMSO (final concentration ranging from $1.00\times10^{-3}$ M to $1.56\times10^{-6}$). The concentration of the enzyme stock solution was 150 nM in assay buffer (final concentration: 30.0 nM).

Caspase-3.

Caspase-3 kinetic assays were performed using Ac-DEVD-AMC ($K_m$=9.7 µM) as the substrate and with the same conditions as described for Caspase-2. The concentration of the substrate stock solution was 194 µM in assay buffer (final concentration: 9.7 µM). The inhibitor stock solutions ranged from $1.50\times10^{-8}$ M to $2.88\times10^{-4}$ M in DMSO (final concentration ranging from $7.50\times10^{-9}$ M to $1.44\times10^{-5}$ M). The concentration of the enzyme stock solution was 3.75 nM in assay buffer (final concentration: 0.75 nM).

Caspase-5.

Caspase-5 kinetic assays were performed using Ac-WEHD-AMC ($K_m$=15.0 µM) as the substrate and with the same conditions as described for Caspase-1. The concentration of the substrate stock solution was 300 µM in assay buffer (final concentration: 15.0 µM). The inhibitor stock solutions ranged from $2.00\times10^{-6}$ M to $4.80\times10^{-4}$ M in DMSO (final concentration ranging from $1.00\times10^{-7}$ M to $2.4\times10^{-5}$ M). The concentration of the enzyme stock solution 5% (v/v) in assay buffer (final concentration: 1% (v/v)).

Caspase-6.

Caspase-6 kinetic assays were performed using Ac-DEVD-AMC ($K_m$=236.35 µM) as the substrate and with the same conditions as described for Caspase-3. The concentration of the substrate stock solution was 4.72 mM in assay buffer (final concentration: 236.35 µM). The inhibitor stock solutions ranged from $4.00\times10^{-7}$ M to $4.80\times10^{-4}$ M in DMSO (final concentration ranging from $2.00\times10^{-8}$ M to $1.60\times10^{-6}$ M). The concentration of the enzyme stock solution was 18.75 nM in assay buffer (final concentration: 3.75 nM).

Caspase-7.

Caspase-7 kinetic assays were performed using Ac-DEVD-AMC ($K_m$=20.2 µM) as the substrate and with the same conditions as described for Caspase-3. The concentration of the substrate stock solution was 404 µM in assay buffer (final concentration: 20.2 µM). The inhibitor stock solutions ranged from $4.00\times10^{-7}$ M to $1.28\times10^{-4}$ M in DMSO (final concentration ranging from $2.00\times10^{-8}$ M to $6.40\times10^{-6}$ M). The concentration of the enzyme stock solution was 18.75 nM in assay buffer (final concentration: 3.75 nM).

Caspase-8.

Caspase-8 kinetic assays were performed using Ac-DEVD-AMC ($K_m$=6.79 µM) as the substrate and with the same conditions as described for Caspase-3. The concentration of the substrate stock solution was 135.8 µM in assay buffer (final concentration: 6.79 µM). The inhibitor stock solutions ranged from $3.60\times10^{-6}$ M to $2.30\times10^{-4}$ M in DMSO (final concentration ranging from $1.80\times10^{-8}$ M to $1.15\times10^{-5}$ M). The concentration of the enzyme stock solution was 187.5 nM in assay buffer (final concentration: 32 nM).

Caspase-9.

Caspase-9 kinetic assays were performed using Ac-LEHD-AFC ($K_m$=114 µM) as the substrate and with the same conditions as described for Caspase-1 using the following: The assay buffer was 200 mM HEPES, 100 mM NaCl, 0.01% (w/v) CHAPS, 20% (w/v) sucrose, 20 mM DTT, and 2 mM EDTA in $H_2O$ at pH 7.0 and supplemented with 0.7 M sodium citrate. The concentration of the substrate stock solution was 2.28 mM in assay buffer (final concentration: 114 µM). The inhibitor stock solutions ranged from $4.80\times10^{-6}$ M to $6.40\times10^{-4}$ M in DMSO (final concentration ranging from $2.40\times10^{-7}$ M to $3.20\times10^{-5}$ M). The concentration of the enzyme stock solution was 200 nM in assay buffer (final concentration: 40.0 nM).

Example 2

Novel Caspase Inhibitors Rescue Cell Death in Huntington's Disease Models

Abstract

Huntington's disease (HD) is an autosomal-dominant progressive neurodegenerative disorder leading to loss of function and viability of neurons in the striatum and cortex. Proteolysis of mutant huntingtin (Htt) may be a critical molecular event triggering the selective neuronal loss. Caspase cleavage of mutant Htt has been shown to correlate with cytotoxicity in HD cell culture and mouse models and most recently, caspase-6 cleavage of mutant Htt has been shown to play a key role in HD pathogenesis in a full-length Htt mouse model of HD (YAC128; Graham et al., 2006). Given the strong evidence for the toxic fragment hypothesis in HD, we used a fragment-based non-peptidic protease substrate library to screen for caspase-2, -3 and caspase-6 inhibitors. Substrate activity screening (SAS), a fragment-based identification method yielded three novel, low-molecular weight substrates that were optimized and converted from substrates to potent, non-peptidic inhibitors of caspase-3 and -6 (MJL-001i, MJL-002i, MJL-003i. MJL-001i, MJL-002i, MJL-003i (1-100 nM) suppressed Hdh111Q mediated toxicity and blocked proteolysis of Htt at amino acid 513 (caspase-3 site) and 586 (caspase-6 site). Currently these compounds are being evaluated in HD mouse models.

Introduction

Figure 11:
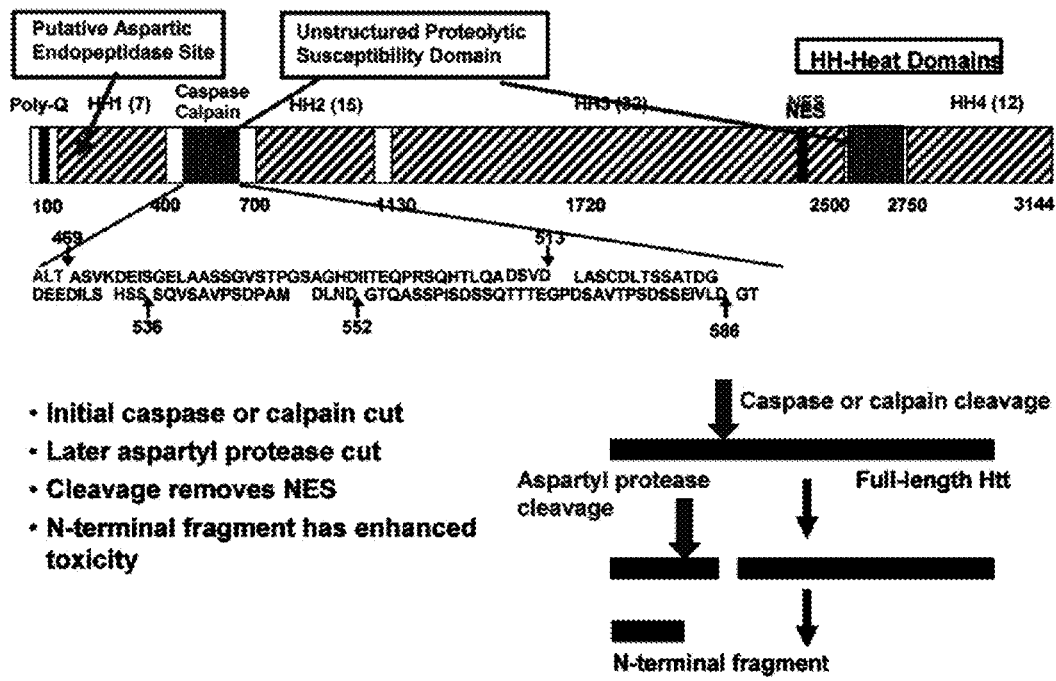
FIG. 11 shows a schematic of Htt proteolysis. Htt (SEQ ID NO:1).

Huntingtin is cleaved by caspases and calpains. In vitro, Htt is cleaved at amino acid 513, 552 by caspase-3/-7, 552 by caspase-2 and 586 by caspase-6. Huntingtin is also cleaved by calpains at amino acid 469 and 536 (FIG. 11). Since proteolysis of Htt by caspases appears to play a critical role in HD disease pathogenesis and progression we screened for caspase inhibitors.

Substrate Activity Screening

A fragment-based method for the rapid development of novel substrates and their conversion into non-peptidic inhibitors of Cys and Ser proteases.

Addresses two key challenges in fragment-based screening: 1) The accurate and efficient identification of weak binding fragments; and 2) The rapid optimization of the initial weak binding fragments into higher-affinity compounds.

FIG. 12 shows a schematic of SAS approach. As illustrated therein, in certain embodiments of this approach, (1) a library of N-acyl aminocoumarins with diverse, low molecular weight N-acyl groups is screened to identify protease substrates using a simple fluorescence-based assay, (2) the identified N-acyl aminocoumarin substrates are optimized by rapid analogue synthesis and evaluation, and (3) the optimized substrates are converted to inhibitors by direct replacement of the aminocoumarin with known mechanism-based pharmacophores.

Non-Peptidic Inhibitors.

A number of non-peptidic caspase inhibitors were identified. A few illustrative inhibitors are shown in Table 2.

Production of Htt Using NeoAntibodies.

Figure 13A:
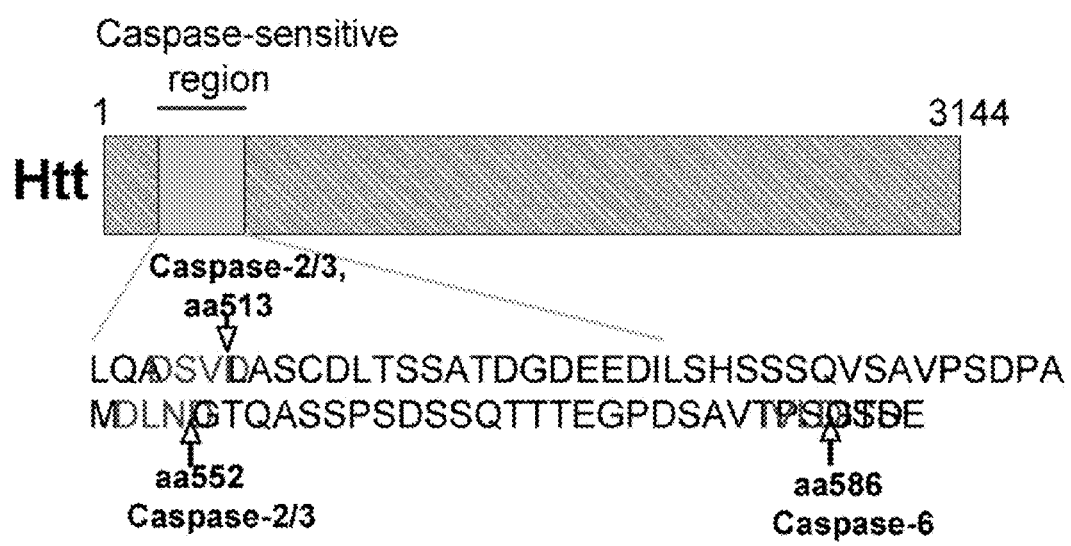
Figure 13C:
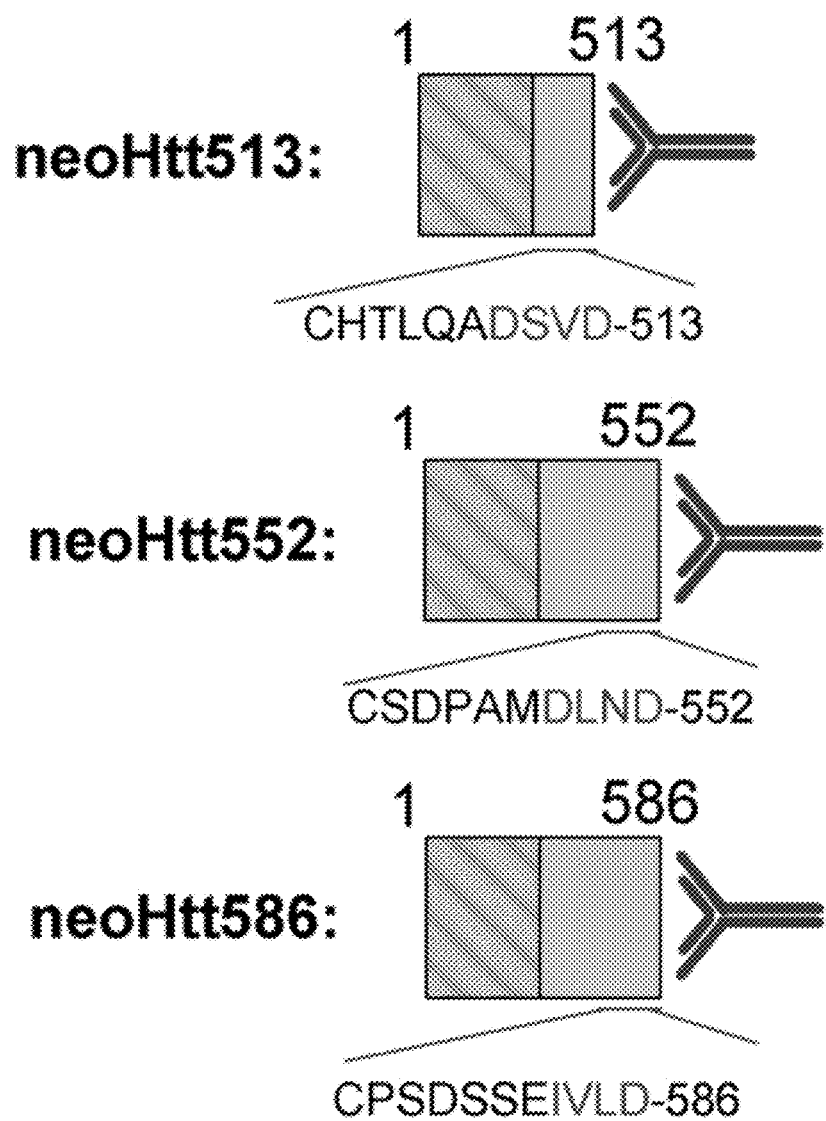

FIG. 13A shows a diagram of identified caspase cleavage sites in Htt. Caspase recognition sequences are marked in red and caspases that cleave at each site are indicated along with the amino acid number. FIG. 13B shows a table of neoepitope antibodies produced to caspase cleavage sites in Htt. FIG. 13C shows a diagram of the antibody recognition sequences of the four neoepitope antibodies used in this study.

Specificity of Neoepitope Antibodies.

Figure 14:
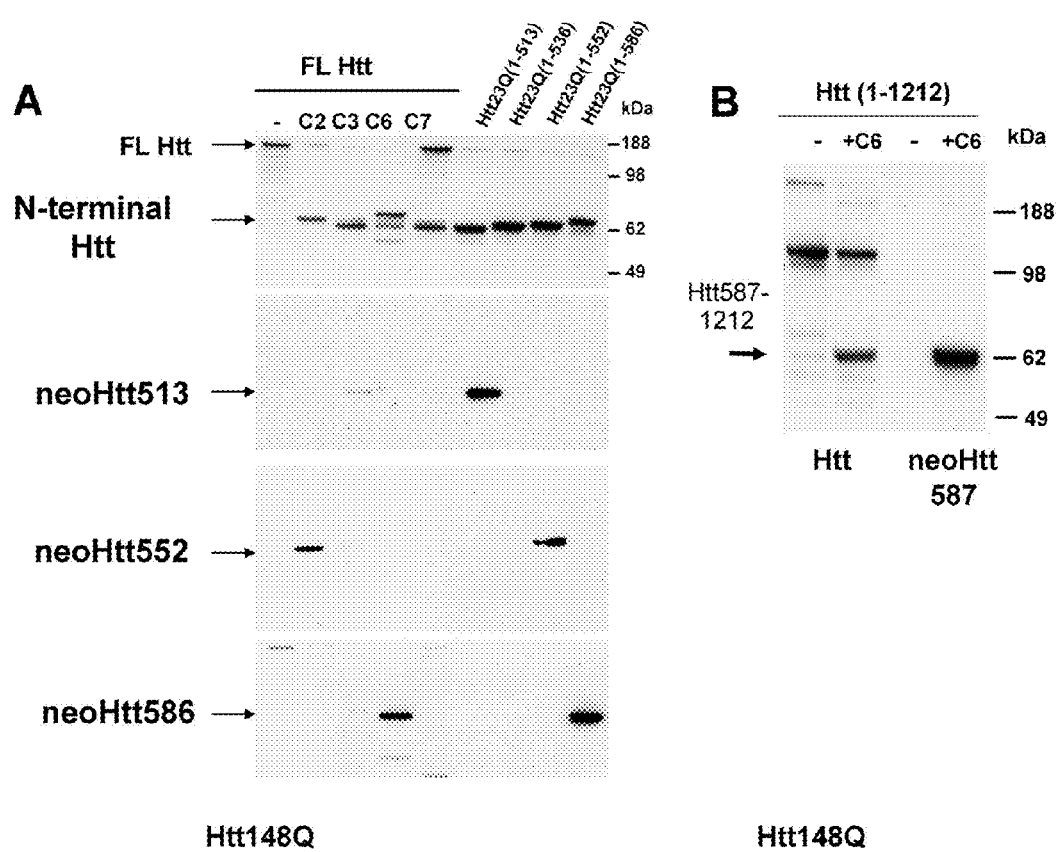
FIGS. 14A and 14B show the specificity of neoepitope antibodies.

FIG. 14, panel A shows blots with full-length huntingtin (23Q) expressing cell lysates cleaved with caspase-2, -3, -6 or -7 and Htt stop constructs (23Q) ending in amino acid 513, 552 or 586 were probed with Htt antibody (2166), neoHtt513, neoHtt552 or neoHtt586. FIG. 14, panel B shows blots with N-terminal huntingtin (amino acids 1-1212, 15Q) expressing cell lysates +/–caspase-6 were probed with a Htt antibody to amino acids 1171-1177 (left panel) or neoHtt586 (right panel). neoHtt586 has no non-specific reactivity.

Evaluation of Htt Proteolysis with MJL-001i, MJL-002i, MJL-003i.

Figure 15:
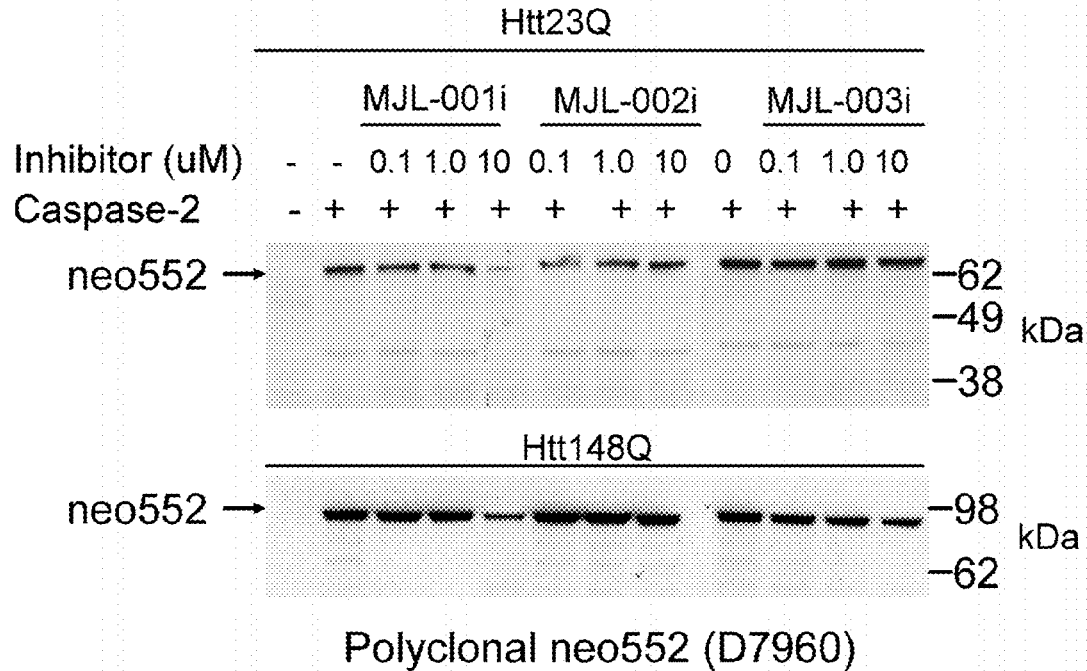
FIG. 15 shows blots with full-length huntingtin (23Q & 148Q) treated with caspase-2 along with inhibitors MJL-001i, MJL-002i, and MJL-003i at varied concentrations (0.1 µM, 1.0 µM and 10 µM) Inhibitors MJL001i and MJL-003i show slight inhibition at the higher concentration of 10 µM.

FIG. 15 shows blots with full-length huntingtin (23Q & 148Q) treated with caspase-2 along with inhibitors MJL-001i, MJL-002i, and MJL-003i at varied concentrations (0.1 uM, 1.0 uM and 10 uM) Inhibitors MJL001i and MJL-003i show slight inhibition at the higher concentration of 10 uM.

Figure 16:
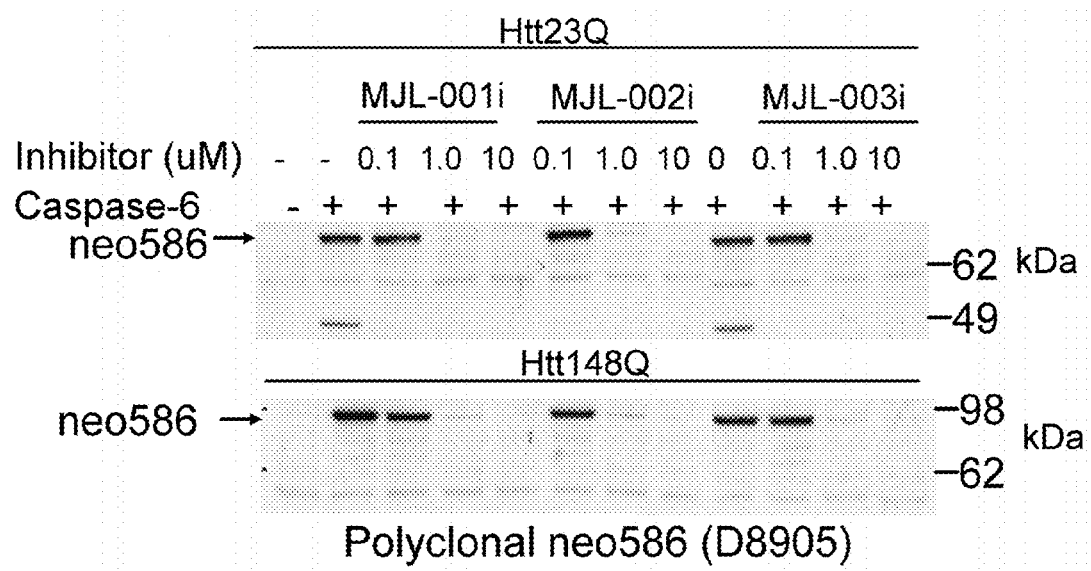
FIG. 16 shows Blots with full-length huntingtin (23Q & 148Q) treated with caspase-6 along with inhibitors MJL-001i, MJL-002i, and MJL-003i at varied concentrations (0.1 µM, 1.0 µM and 10 µM). All inhibitors showed inhibition at concentrations 1.0 µM and 10 µM.

FIG. 16 shows blots with full-length huntingtin (23Q & 148Q) treated with caspase-6 along with inhibitors MJL-001i, MJL-002i, and MJL-003i at varied concentrations (0.1 uM, 1.0 uM and 10 uM). All inhibitors showed inhibition at concentrations 1.0 uM and 10 uM.

Figure 17:
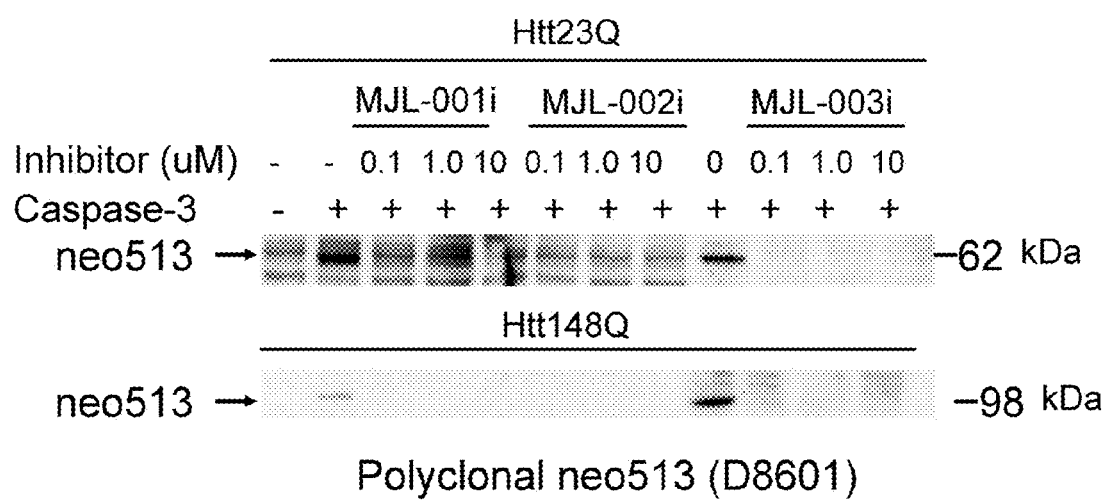
FIG. 17 shows blots with full-length huntingtin (23Q & 148Q) treated with Caspase 3 along with inhibitors MJL-001i, MJL-002i, and MJL-003i at varied concentrations (0.1 µM, 1.0 µM and 10 µM). All three inhibitors showed inhibition at concentrations 0.1 µM, 1.0 µM, and 10 µM.

FIG. 17 shows blots with full-length huntingtin (23Q & 148Q) treated with Caspase 3 along with inhibitors MJL-001i, MJL-002i, and MJL-003i at varied concentrations (0.1 uM, 1.0 uM and 10 uM). All three inhibitors showed inhibition at concentrations 0.1 uM, 1.0 uM, and 10 uM.

Evaluation of MJL-001i, MJL-002i, MJL-003i in Hdh111Q Cells.

Figure 18:
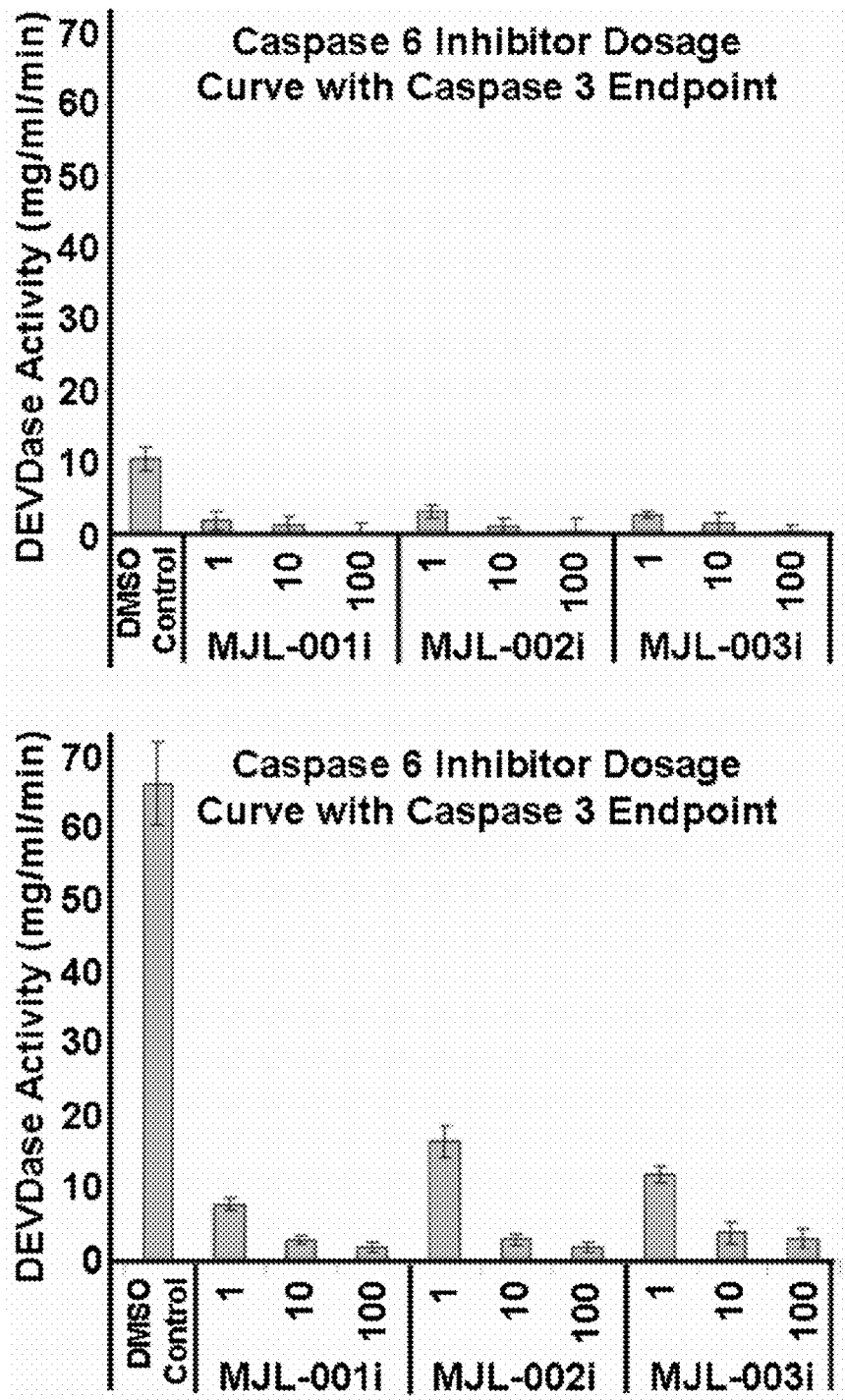
FIG. 18 shows that caspase inhibitors described herein block caspase activation.

FIG. 18 shows the results of an evaluation of the activity of MJL-001i, MJL-002i, MJL-003i in Hdh111Q cells.

CONCLUSIONS

SAS screening identified three novel caspase inhibitors MJL-001i, MJL-002i, and MJL-003i.

MJL-001i, MJL-002i, and MJL-003i are affective at blocking the cleavage of Htt at amino acid 513 and 586 mediated by caspase-3 or caspase-6.

MJL-001i, MJL-002i, and MJL-003i do not inhibit caspase-2 cleavage of Htt.

MJL-001i, MJL-002i, and MJL-003i block caspase activation in Hdh111Q cells. MJL-003i was most potent.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A caspase substrate of formula VIII or its pharmaceutically acceptable salt:

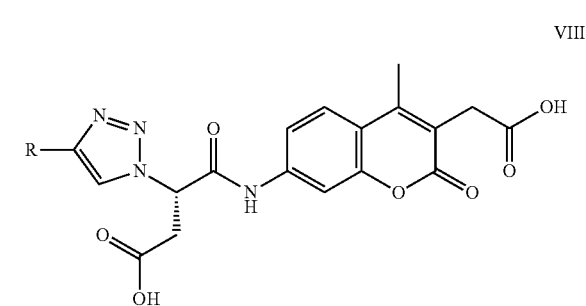

VIII wherein:
R is alkyl, alkoxy, aryl, heteroaryl, cycloalkyl, heterocycle, substituted alkyl, substituted cycloalkyl, and substituted heterocycle; and said substrate is ineffectively or efficiently cleaved by a caspase selected from the group consisting of caspase-1, caspase-2, caspase-3, caspase-5, caspase-6, caspase-7, caspase-8, and caspase-9.

2. The substrate of claim 1, wherein R is selected from the group consisting of

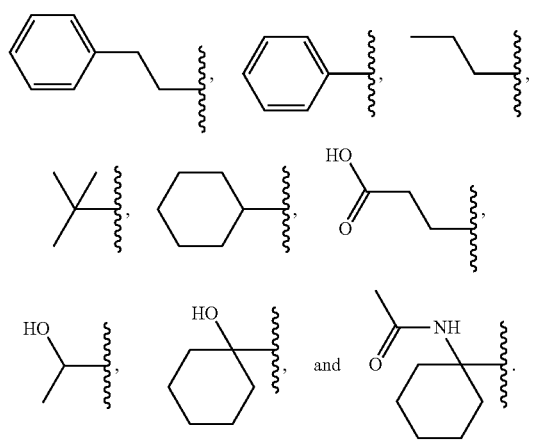
3. The substrate of claim 1, wherein R is selected from the group consisting of
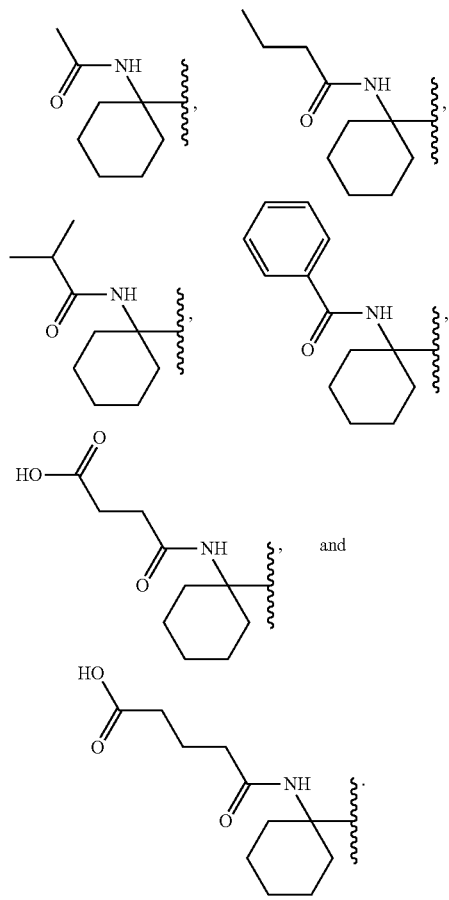
4. The substrate of claim 1, wherein R is selected from the group consisting of
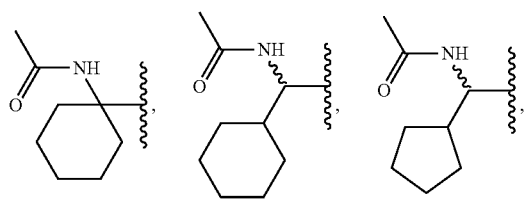
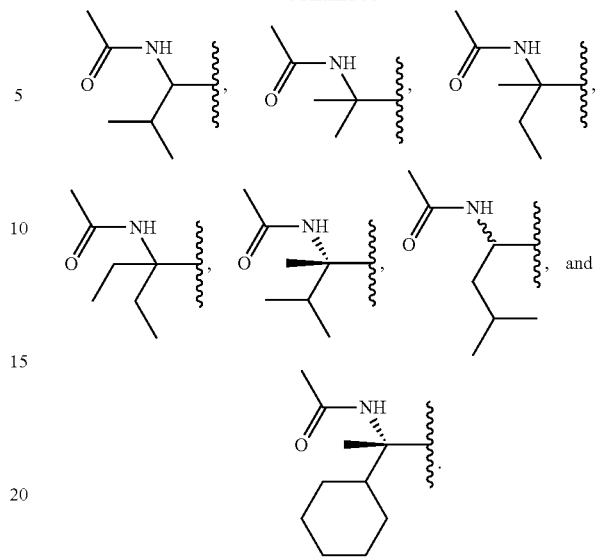
5. The substrate of claim 1, wherein R is selected from the group consisting of
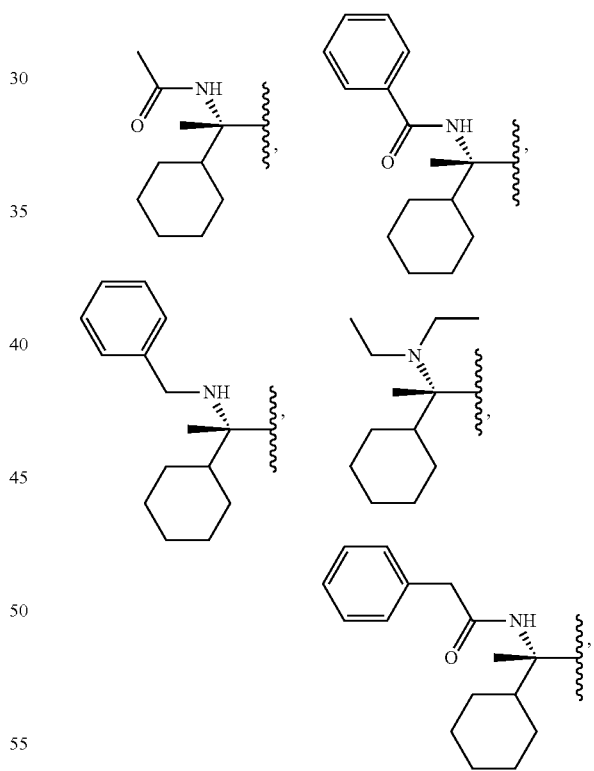
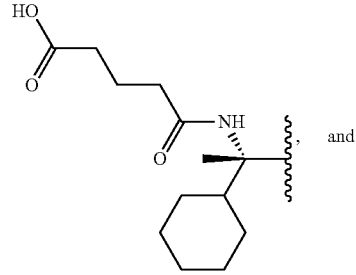

-continued
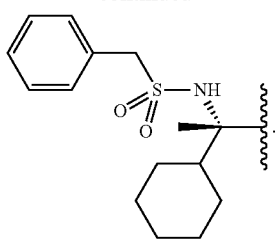
6. The substrate of claim 1, wherein R is selected from the group consisting of
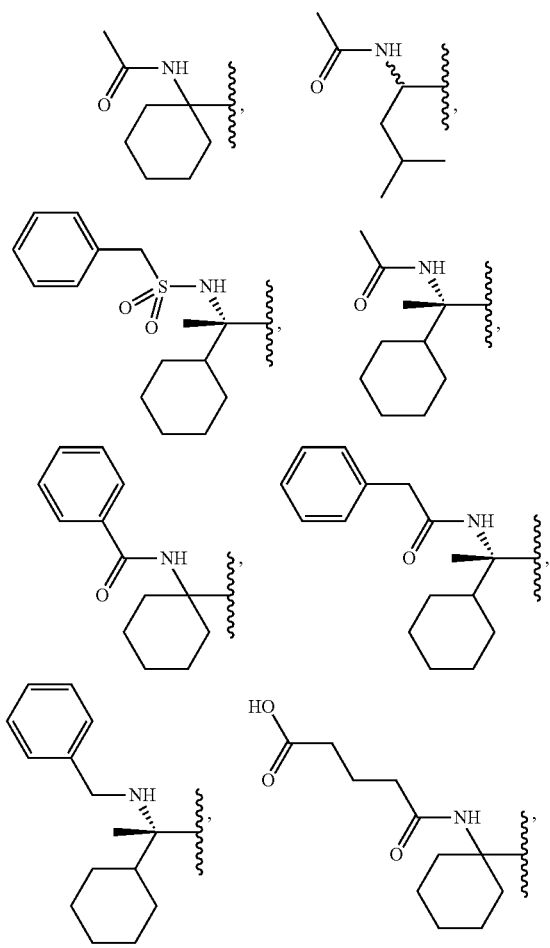
-continued
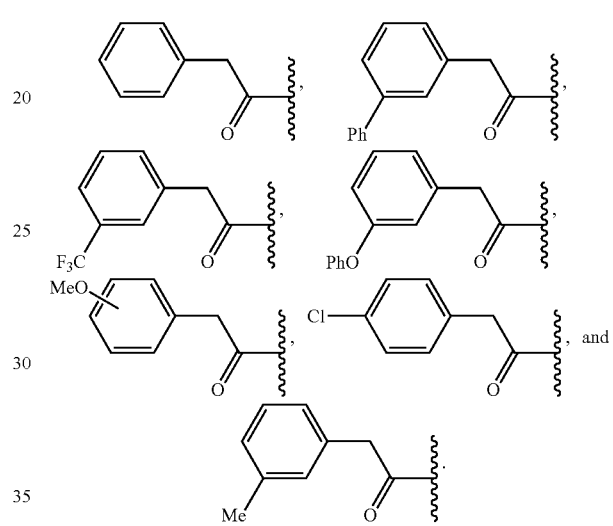
7. The substrate of claim 1, wherein R is selected from the group consisting of
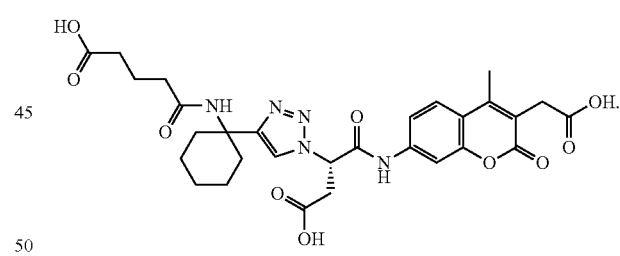
8. The substrate of claim 1, wherein said substrate has the formula:
* * * * *

UNITED STATES PATENT AND TRADEMARK OFFICE
CERTIFICATE OF CORRECTION

PATENT NO. : 9,245,290 B2
APPLICATION NO. : 13/968338
DATED : January 26, 2016
INVENTOR(S) : Lisa M. Ellerby, Jonathan A. Ellman and Melissa J. Leyva It is certified that error appears in the above-identified patent and that said Letters Patent is hereby corrected as shown below:

In the Specification

Column 1, Line 15-17, change "This work was supported in part by Grant Nos: NS40251 and GM54051 from the National Institutes of Health. The Government has certain rights in this invention." to --This invention was made with Government support under grant nos. NS040251 and GM054051 awarded by The National Institutes of Health. The Government has certain rights in this invention.--.

Signed and Sealed this
Twenty-fifth Day of April, 2023

Katherine Kelly Vidal
*Director of the United States Patent and Trademark Office*